US005580736A

United States Patent [19]
Brent et al.

[11] Patent Number: 5,580,736
[45] Date of Patent: Dec. 3, 1996

[54] INTERACTION TRAP SYSTEM FOR ISOLATING NOVEL PROTEINS

[75] Inventors: Roger Brent, Cambridge; Jenö Gyuris, Arlington; Erica Golemis, Somerville, all of Mass.

[73] Assignee: The General Hospital Corporation, Boston, Mass.

[21] Appl. No.: 370,225

[22] Filed: Jan. 9, 1995

Related U.S. Application Data

[63] Continuation of Ser. No. 969,038, Oct. 30, 1992, abandoned.
[51] Int. Cl.$^6$ ............................. C12Q 1/68; C12N 15/63; C12N 15/00
[52] U.S. Cl. ...................... 435/6; 435/172.3; 435/320.1; 435/69.1; 435/254.2; 530/358; 536/23.5
[58] Field of Search ....................... 435/6, 69.1, 172.3, 435/320.1, 255; 530/358; 536/23.5

[56] References Cited

U.S. PATENT DOCUMENTS 5,283,173  2/1994  Fields et al. ............................. 435/6

OTHER PUBLICATIONS

Gyuris et al., Cell 75:791–803 (1993).
Hannon et al., Proc. Natl. Acad. Sci. USA 91:1731–1735 (1994).
Yang et al., Science 257:680–682 (1992).
Dalton and Treisman, Cell 68:597–612, 1992.
Touchette, The Journal of NIH Research 3:44–46, 1991.
Chien et al., Proc. Natl. Acad. Sci. USA 88:9578–9582, 1991.
Fields and Song, Nature 340:245–246, 1989.
Broach et al., "Transformation in Yeast: Development of a Hybrid Cloning Vector and Isolation of the CAN1 Gene;" Gene 8, 121–133, 1979.
Celenza et al., "A Yeast Gene That is Essential for Release from Glucose Repression Encodes a Protein Kinase;" Science 233, 1175–1180, 1986.
Celenza et al., "Molecular Analysis of the SNF4 Gene of Saccharomyces cerevisiae: Evidence for Physical Association of the SNF4 Protein with . . . " Molecular and Cellular Biology 9, 5045–5054, 1989.
Celenza et al., "Mutational Analysis of the Saccharomyces cerevisiae SNF1 Protein Kinase and Evidence for Functional Interaction with the SNF4 Protein;" Molecular and Cellular Biology 9, 5034–5044, 1989.
Curran et al., "Fos and Jun: The AP–1 Connection;" Cell 55, 395–397, 1988.
Dang et al., "Intracellular Leucine Zipper Interactions Suggest c–Myc Hetero–Oligomerization;" Molecular and Cellular Biology 11, 954–962, 1991.
Furey et al., "Crystal Structure of Cd, Zn Metallothioein;" Science 231, 704–707, 1986.
Gill et al., "Mutants of GAL4 Protein Altered in an Activation Function;" Cell 51, 121–126, 1987.
Goff et al., "Functional Analysis of the Transcriptional Activator Encoded by the Maize B Gene: Evidence for a Direct Functional Interaction . . . ;" Genes & Development 6, 864–875, 1992.

Hardy et al., "A RAPt1–Interacting Protein Involved in Transcriptional Silencing and Telomere Length Regulation;" Genes & Development 6, 801–814, 1992.
Hope et al., "Functional Dissection of a Eukaryotic Transcriptional Activator Protein, GCN4 of Yeast;" Cell 46, 885–894, 1986.
Hope et al., "Structural and Functional Characterization of the Short Acidic Transcriptional Activation Region of Yeast GCN4 Protein;" Nature 333, 635–640, 1988.
Hu et al., "Sequence Requirements for Coiled–Coils: Analysis with Repressor–GCN4 Leucine Zipper Fusions;" Science 250, 1400–1403, 1990.
Johnston, "A Model Fungal Gene Regulatory Mechanism: The GAL Genes of Saccharomyces Cerevisiae;" Microbiological Reviews 51, 458–476, 1987.
Keegan et al., "Separation of DNA Binding from the Transcription–Activating Function of a Eukaryotic Regulatory Protein;" Science 231, 699–704, 1986.
Kumar et al., "Functional Domains of the Human Estrogen Receptor;" Cell 51, 941–951, 1987.
Laughon et al., "Primary Structure of the Saccharomyces Cerevisiae GAL4 Gene;" Molecular and Cellular Biology 4, 260–267 1984.
Ma et al., "Converting a Eukaryotic Transcriptional Inhibitor into an Activator;" Cell 55, 443–446, 1988.
Ma et al., "Deletion Analysis of GAL4 Defines Two Transcriptional Activating Segments;" Cell 48, 847–853, 1987.
Martin et al., "Genetic Exploration of Interactive Domains in RNA Polymerase II Subunits;" Molecular and Cellular Biology 10, 1908–1914, 1990.
McKnight et al., "Binding of the Virion Protein Mediating Gene Induction in Herpes Simplex Virus 1–Infected Cells to its Cis Site Requires Cellular Proteins;" Proc. Natl. Acad. Sci. USA 84, 7061–7065, 1987.
Silver et al., "Amino Terminus of the Yeast GAL4 Gene Product is Sufficient for Nuclear Localization;" Proc. Natl. Acad. Sci. USA 81, 5951–5955, 1984.

(List continued on next page.)

*Primary Examiner*—Robert A. Wax
*Assistant Examiner*—Rebecca Prouty
*Attorney, Agent, or Firm*—Fish & Richardson P.C.

[57] ABSTRACT

Disclosed is a method for determining whether a first protein is capable of physically interacting with a second protein. The method involves: (a) providing a host cell which contains (i) a reporter gene operably linked to a protein binding site; (ii) a first fusion gene which expresses a first fusion protein, the first fusion protein including the first protein covalently bonded to a binding moiety which is capable of specifically binding to the protein binding site; and (iii) a second fusion gene which expresses a second fusion protein, the second fusion protein including the second protein covalently bonded to a weak gene activating moiety; and (b) measuring expression of the reporter gene as a measure of an interaction between the first and the second proteins. Such a determination facilitates the isolation of the gene encoding the interacting protein. Also disclosed herein is recombinant Cdi1 polypeptide, nucleic acid encoding the Cdi1 polypeptide, and uses thereof.

41 Claims, 13 Drawing Sheets

OTHER PUBLICATIONS

Thukral et al., "Localization of a Minimal Binding Domain and Activation Regions in Yeast Regulatory Protein ADR1;" Molecular Biology, 9, 2360–2369, 1988.

Wittekind et al., "Isolation and Characterization of Temperature–Sensitive Mutations in RPA190, the Gene Encoding the Largest Subunit of RNA Polymerase . . . ;" Molecular and Cellular Biology 8, 3997–4008, 1988.

Meyerson et al., The EMBO Journal 11:2909–2917, 1992.

Yang et al., Science 257:680–682, 1992.

Koff et al., Cell 66:1217–1228, 1991.

Tsai et al., Nature 353:174–177, 1991.

Xiong et al., Cell 65:691–699, 1991.

Draetta, Trends in Biochem. Sci. 15:378–382, 1990.

Richardson et al., Genes & Development 4:1332–1344, 1990.

Wittenberg et al., Cell 62:225–237, 1990.

Richardson et al., Cell 59:1127–1133, 1989.

Wittenberg et al., Molecular and Cellular Biology 9:4064–4068, 1989.

Pines et al., Cell 59:833–846, 1989.

Hadwiger et al., Proc. Natl. Acad. Sci. USA 86:6255–6259, 1989.

Wittenberg et al., Cell 54:1061–1072, 1988.

Gill et al., Nature 334:721–724, 1988.

Brent et al., Nature 312:612–615, 1984.

Brent et al., 1985. Cell 43:729–736.

J. Ma et al. "A New Class of Yeast Transcriptional Activators" Cell 51:113–119 (Oct. 1987).

S. L. Berger et al. "Genetic Isolation of ADA2: A Potential Transcriptional Adaptor Required for function of Certain Acidic Activation Domains." Cell 70:251–265 (Jul. 1992).

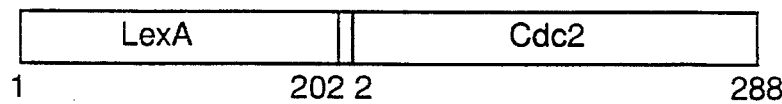
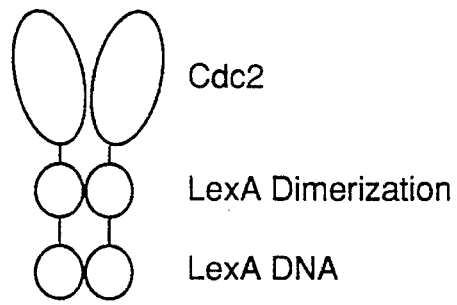
FIG. 3A
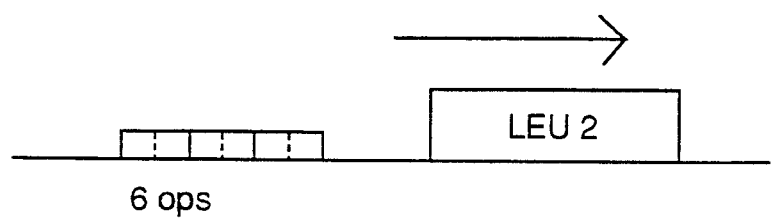
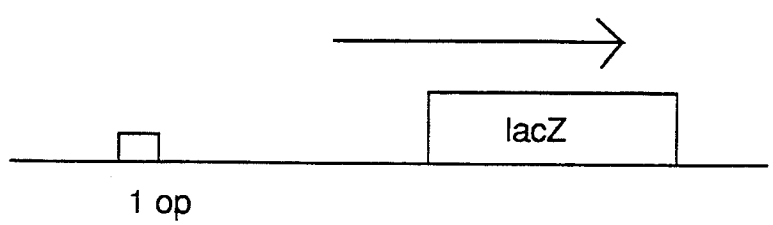
FIG. 3B

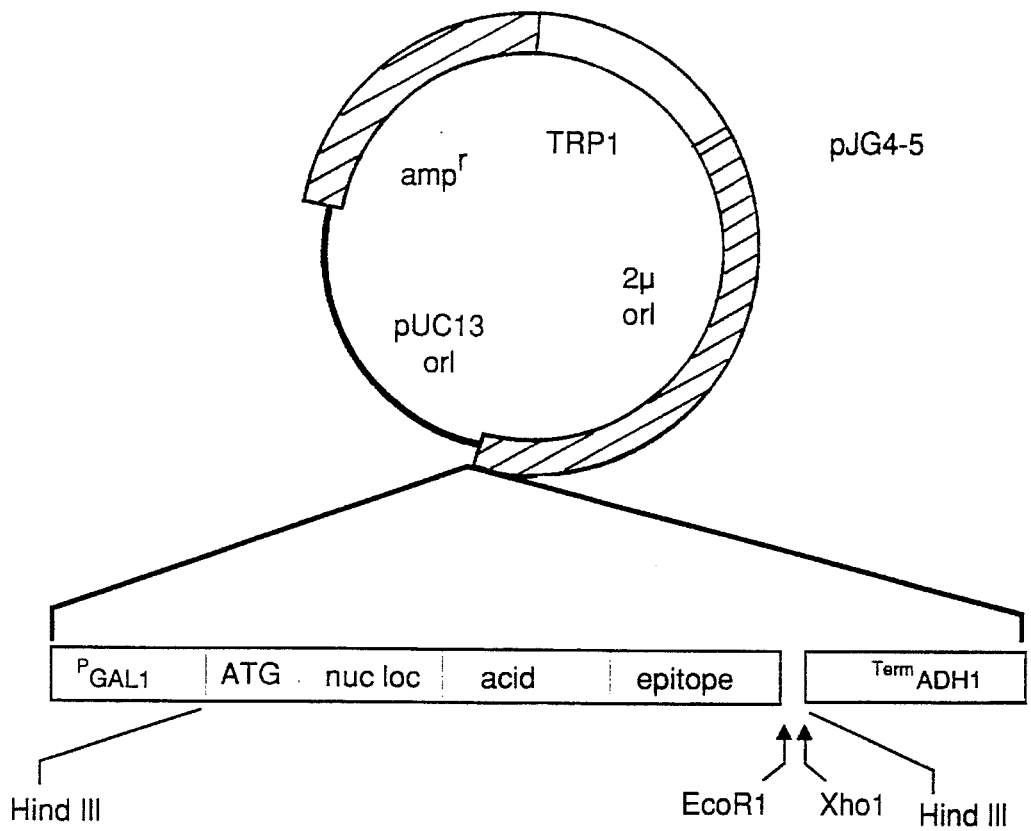

```
1    AAG CTT ATG GGT GCT CCT CCA AAA AAG AAG AGA AAG GTA GCT GGT
1            M   G   A   P   P   K   K   K   R   K   V   A   G

46   ATC AAT AAA GAT ATC GAG GAG TGC AAT GCC ATC ATT GAG CAG TTT
14   I   N   K   D   I   E   E   C   N   A   I   I   E   Q   F

91   ATC GAC TAC CTG CGC ACC GGA CAG GAG ATG CCG ATG GAA ATG GCG
29   I   D   Y   L   R   T   G   Q   E   M   P   M   E   M   A

136  GAT CAG GCG ATT AAC GTG GTG CCG GGC ATG ACG CCG AAA ACC ATT
44   D   Q   A   I   N   V   V   P   G   M   T   P   K   T   I

181  CTT CAC GCC GGG CCG CCG ATC CAG CCT GAC TGG CTG AAA TCG AAT
59   L   H   A   G   P   P   I   Q   P   D   W   L   K   S   N

226  GGT TTT CAT GAA ATT GAA GCG GAT GTT AAC GAT ACC AGC CTC TTG
74   G   F   H   E   I   E   A   D   V   N   D   T   S   L   L

271  CTG AGT GGA GAT GCC TCC TAC CCT TAT GAT GTG CCA GAT TAT GCC
89   L   S   G   D   A   S   Y   P   Y   D   V   P   D   Y   A

316  TCT CCC GAA TTC GGC CGA CTC GAG AAG CTT
104  S   P   E   F
```

FIG. 3C

```
                       -31  C GGC ACT GGT CTC GAC GTG GGG CGG CCA GCG

1    ATG GAG CCG CCC AGT TCA ATA CAA ACA AGT GAG TTT GAC TCA TCA GAT
  1     M   E   P   P   S   S   I   Q   T   S   E   F   D   S   S   D

49    GAA GAG CCT ATT GAA GAT GAA CAG ACT CCA ATT CAT ATA TCA TGG CTA
 17     E   E   P   I   E   D   E   Q   T   P   I   H   I   S   W   L

97    TCT TTG TCA CGA GTG AAT TGT TCT CAG TTT CTC GGT TTA TGT GCT CTT
 33     S   L   S   R   V   N   C   S   Q   F   L   G   L   C   A   L

145    CCA GGT TGT AAA TTT AAA GAT GTT AGA AGA AAT GTC CAA AAA GAT ACA
 49     P   G   C   K   F   K   D   V   R   R   N   V   Q   K   D   T

193    GAA GAA CTA AAG AGC TGT GGT ATA CAA GAC ATA TTT GTT TTC TGC ACC
 65     E   E   L   K   S   C   G   I   Q   D   I   F   V   F   C   T

241    AGA GGG GAA CTG TCA AAA TAT AGA GTC CCA AAC CTT CTG GAT CTC TAC
 81     R   G   E   L   S   K   Y   R   V   P   N   L   L   D   L   Y

289    CAG CAA TGT GGA ATT ATC ACC CAT CAT CAT CCA ATC GCA GAT GGA GGG
 97     Q   Q   C   G   I   I   T   H   H   H   P   I   A   D   G   G

337    ACT CCT GAC ATA GCC AGC TGC TGT GAA ATA ATG GAA GAG CTT ACA ACC
113     T   P   D   I   A   S   C   C   E   I   M   E   E   L   T   T

385    TGC CTT AAA AAT TAC CGA AAA ACC TTA ATA CAC TGC TAT GGA GGA CTT
129     C   L   K   N   Y   R   K   T   L   I   H   C   Y   G   G   L

432    GGG AGA TCT TGT CTT GTA GCT GCT TGT CTC CTA CTA TAC CTG TCT GAC
145     G   R   S   C   L   V   A   A   C   L   L   L   Y   L   S   D

481    ACA ATA TCA CCA GAG CAA GCC ATA GAC AGC CTG CGA GAC CTA AGA GGA
161     T   I   S   P   E   Q   A   I   D   S   L   R   D   L   R   G

529    TCC GGG GCA ATA CAG ACC ATC AAG  CAA TAC AAT TAT CTT CAT GAG TTT
177     S   G   A   I   Q   T   I   K   Q   Y   N   Y   L   H   E   F

577    CGG GAC AAA TTA GCT GCA CAT CTA TCA TCA AGA GAT TCA CAA TCA AGA
192     R   D   K   L   A   A   H   L   S   S   R   D   S   Q   S   R

625    TCT GTA TCA AGA TAA AGG AAT TCA AAT AGC ATA TAT ATG ACC ATG TCT
209     S   V   S   R   *

673    GAA ATG TCA GTT CTC TAG CAT AAT TTG TAT TGA AAT GAA ACC ACC AGT

721    GTT ATC AAC TTG AAT GTA AAT GTA CAT GTG CAG ATA TTC CTA AAG TTT

769    TAT TGA C
```

FIG. 6

FIG. 8A
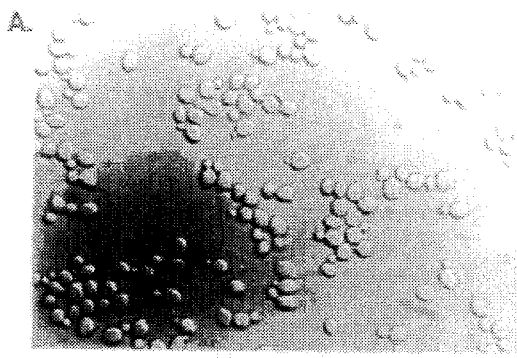
FIG. 8C
FIG. 8B
FIG. 8D
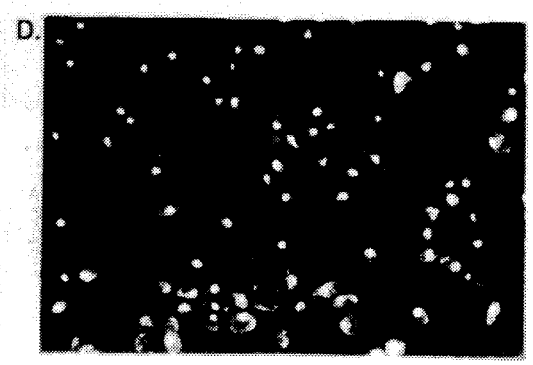
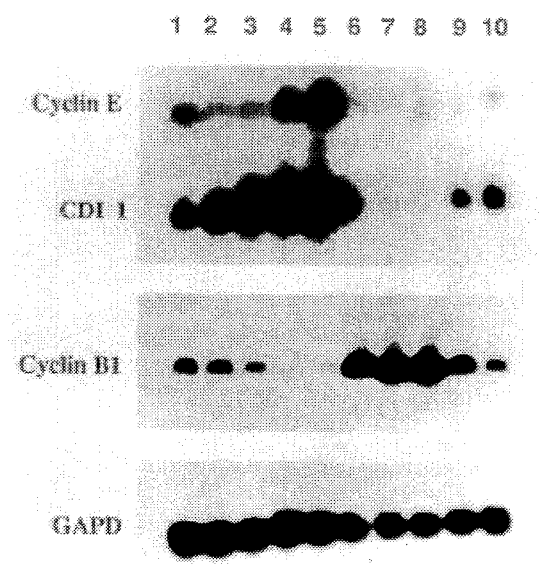
FIG. 9A

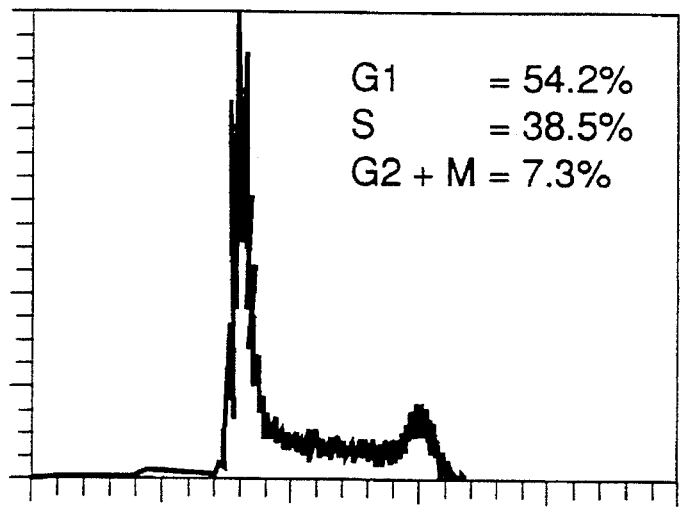
CONTROL
G1 = 54.2%
S = 38.5%
G2 + M = 7.3%
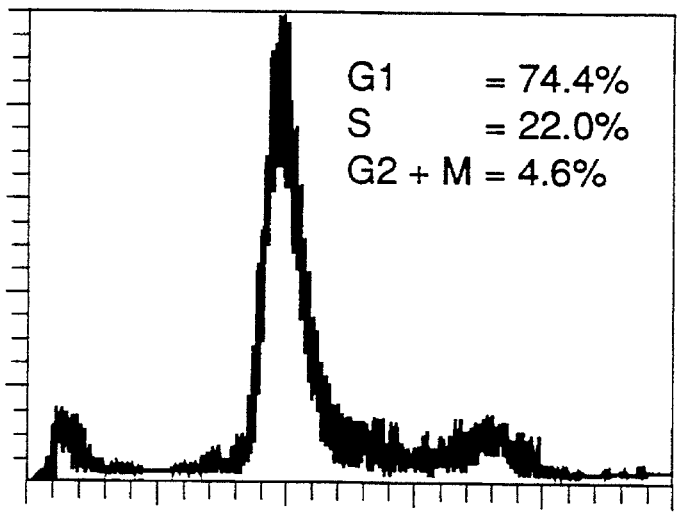
CDI1
G1 = 74.4%
S = 22.0%
G2 + M = 4.6%

```
                                                               57
                                                                *
HsCdc2    M EDYTKIEKIG EGTYGVVYKG RHKTTGQ.... VVAMKKIRLE SEEEGVPSTA IREISLLKEL RHPNIVSLQD VLMQD..... (SEQ ID NO:9)
HsCdk2    M ENFQKVEKIG EGTYGVVYKA RNKLTGE.... VVALKKIRLD TETEGVPSTA IREISLLKEL NHPNIVKLLD VIHTE..... (SEQ ID NO:10)
ScCdc28   MSGEL ANYKRLEKVG EGTYGVVYKA LDLRPGQGQR VVALKKIRLE SEDEGVPSTA IREISLLKEL KDDNIVRLYD IVHSDA.... (SEQ ID NO:11)
DmCdc2    M EDFEKIEKIG EGTYGVVYKG RNRLTGQ.... IVAMKKIRLE SDDEGVPSTA IREISLLKEL KHENIVCLED VLMEE..... (SEQ ID NO:12)
DmCdc2c   MTTIL DNFQRAEKIG EGTYGIVYKA RSNSTGQ.... DVALKKIRLE GETEGVPSTA IREISLLKNL KHPNVVQLFD VVISG..... (SEQ ID NO:13)
ScFus3    MPKRIVYNIS SDFQLKSLLG EGAYGVVCSA THKPTGE.... IVAIKKIE.P FDKPLFALRT LREIKILKHF KHENIITIFN IQRPDSFENF (SEQ ID NO:14)

78 82                                                            154
           *  *                                                             *
HsCdc2    SRLYLIFEFL SMDLKKYLDS IPPGQYMDSS LVKSYLYQIL QGIVFCHSRR VLHRDLKPQN LLIDDKGTIK LADFGLARAF GIPI..... (SEQ ID NO:15)
HsCdk2    NKLYLVFEFL HQDLKKFMDA SALTG.IPLP LIKSYLFQLL QGLAFCHSHR VLHRDLKPQN LLINTEGAIK LADFGLARAF GVPV..... (SEQ ID NO:16)
ScCdc28   HKLYLVFEFL DLDLKRYMEG IVKKFEMQLC KGIAYCHSHR VLHRDLKPQN ILHRDLKPQN LGDFGLARAF GVPL..... (SEQ ID NO:17)
DmCdc2    NRIYLIFEFL SMDLKKYMDS LPVDKHMESE LVRSYLYQIT SAILFCHRRR VLHRDLKPQN LLIDKSGLIK VADFGLGRSF GIPI..... (SEQ ID NO:18)
DmCdc2c   NNLYMIFEYL NMDLKKLMDK KK.DV.FTPQ LIKSYMHQIL DAVGFCHTNR ILHRDLKPQN LLVDTAGKIK LADFGLARAF NVPM..... (SEQ ID NO:19)
ScFus3    NEVYIIQELM QTDLHRVIS. ...TQMLSDD HIQYFIYQTL RAVKVLHGSN VIHRDLKPSN LLINSNCDLK VCDFGLARII DESAADNSEP (SEQ ID NO:20)

214
                                                    *
HsCdc2    ....RVYTHE VVTLWYRSPE VLLGSARYST PVDIWSIGTI FAELATKKPL FHGDSEIDQL FRIFRALGTP ..NNEVWP.E VESLQDYKNT (SEQ ID NO:21)
HsCdk2    ....RTYTHE VVTLWYRAPE ILLGCKYYST AVDIWSLGCI FAEMVTRRAL FPGDSEIDQL FRIFRTLGTP ..DEVVWP.G VTSMPDYKPS (SEQ ID NO:22)
ScCdc28   ....RAYTHE IVTLWYRAPE VLLGGKQYST GVDTWSIGCI FAEMCNRKPI FSGDSEIDQL FKIFRVLGTP ...NEAIWP.D IVYLPDFKPS (SEQ ID NO:23)
DmCdc2    ....RIYTHE IVTLWYRAPE VLLGSPRYSC PVDIWSIGCI FAEMATRKPL FQGDSEIDQL FKIFRVLGTP ...NEAIWP.D IVYLPDFKPS (SEQ ID NO:24)
DmCdc2c   ....RAYTHE VVTLWYRAPE ILLGTKFYST GVDIWSLGCI FSEMIMRRSL FPGDSEIDQL YRIFRTLSTP ..DETNWP.G VTQLPDFKTK (SEQ ID NO:25)
ScFus3    TGQQSGMTEY VATRWYRAPE VMLTSAKYSR AMDVWSCGCI LAELFLRRPI FPGRDYRHQL LLIFGIIGTP HSDNDLRCIE SPRAREYIKS (SEQ ID NO:26)

256 257
           *  *
HsCdc2    FPKWKPGSLA SHVKNLDENG LDLLSKMLIY DPAKRISGKM ALNHPYFNDL DNQIKKM*      (SEQ ID NO:27)
HsCdk2    FPKWARQDFS KVVPPLDEDG IDLLLDKLLAY DPNKRISAKA ALAHPFFQDV TKPVPHLRL*   (SEQ ID NO:28)
ScCdc28   FPQWRRKDLS QVVPSLDPRG IDLLDKLLAY DPINRISARR AAIHPYFQES *             (SEQ ID NO:29)
DmCdc2    FPQWRRKDLS NQLKNLDANG IDLIQKMLIY DPVHRISAKD ILEHPYFNGF QSGLVRN*     (SEQ ID NO:30)
DmCdc2c   FPRWEGTNMP QPIT..EHEA HELIMSMLCY DPNLRISAKD ALQHAYFRNV .QHVDHVALP VDPNAGSASR LTRLV* (SEQ ID NO:31)
ScFus3    LPMYPAAPLE KMFPRVNPKG IDLLQRMLVF DPAKRITAKE ALEHPYLQTY HDPNDEPEGE PIPPSFFEFD HHKEALTTKD LKKLIWNEIF S*
                                                                                                    (SEQ ID NO:32)
```

FIG. 10

INTERACTION TRAP SYSTEM FOR ISOLATING NOVEL PROTEINS

This is a continuation of application Ser. No. 07/969,038, filed Oct. 30, 1992, now abandoned.

BACKGROUND OF THE INVENTION

This invention was made with Government support awarded by the National Institute of Health. The government has certain rights in the invention. This invention relates to methods for isolating novel proteins. This invention also relates to cancer diagnostics and therapeutics.

In most eukaryotic cells, the cell cycle is governed by controls exerted during G1 and G2. During G2, cells decide whether to enter M in response to relatively uncharacterized intracellular signals, such as those that indicate completion of DNA synthesis (Nurse, Nature 344:503–508, 1990; Enoch and Nurse, Cell 65:921–923, 1991). During G1, cells either enter S or withdraw from the cell cycle and enter a nondividing state known as G0 (Pardee, Science 246:603–608, 1989). While the control mechanisms for these decisions are not yet well understood, their function is clearly central to processes of normal metazoa development and to carcinogenesis.

In yeast, and probably in all eukaryotes, the G1/S and G2/M transitions depend on a family of ~34 kd protein kinases, the Cdc2 proteins, encoded by the $cdc2^+$ (in *S. pombe*) and CDC28 (in *S. cerevisiae*) genes. Cdc2 family proteins from mammalian cells have been also identified. Some including Cdc2 (Lee and Nurse, Nature 327:31–35, 1987), Cdk2 (Elledge and Spotswood, EMBO J. 10:2653–2659, 1991; Tsai et al., Nature 353:174–177, 1991), and Cdk3 (Meyerson et al., EMBO J. 11:2909–2917, 1992) can complement a $cdc28^-$ *S. cerevisiae* for growth.

The activity of the Cdc2 proteins at the G2/M transition point is regulated in two ways: positively, by association with regulatory proteins called cyclins, and negatively, by phosphorylation of a tyrosine near their ATP binding site. At least one of these regulatory mechanisms is operative during G1 (see FIG. 1A). At this time, Cdc2 protein activity is regulated by facultative association with different G1 specific cyclins. In *S. cerevisiae* at least five putative G1 cyclins have been identified in genetic screens, including the products of the CLN1, CLN2, CLN3, HSC26 and CLB5 genes (Cross, Mol. Cell. Biol 8:4675–4684, 1988; Nash et al., EMBO J. 7:4335–4346, 1988; Hadwiger et al., Proc. Nat. Acad. Sci. U.S.A. 86:6255–6259, 1989; and Ogas et al., Cell 66:1015–1026, 1991). The CLN1, CLN2, and CLN3 proteins (here called Cln1, Cln2, and Cln3) are each individually sufficient to permit a cell to make the G1 to S transition (Richardson et al., Cell 59:1127–1133, 1989), and at least one of them (Cln2) associates with Cdc28 in a complex that is active as a protein kinase (Wittenberg et al., Cell 62:225–237, 1990). Recently, putative G1 cyclins have been identified in mammalian cells: Cyclin C, Cyclin D (three forms), and Cyclin E (Koff et al., Cell 66:1217–1228, 1991; Xiong et al., Cell 65:691–699, 1991). Each of these three mammalian cyclins complement a yeast deficient in Cln1, Cln2, and Cln3, and each is expressed during G1.

In *S. cerevisiae*, the synthesis, and in some cases, the activity of the G1 cyclins is under the control of a network of genes that help to couple changes in the extracellular environment to G1 regulatory decisions (FIG. 1A). For example, the SWI4 and SWI6 gene products positively regulate CLN1 and CLN2 transcription and may also positively modulate the activity of Cln3 (Nasmyth and Dirick, Cell 66:995–1013, 1991), the FAR1 product negatively regulates both CLN2 transcription and the activity of its product (Chang and Herskowitz, Cell 63:999–1011, 1990), and the FUS3 product negatively regulates Cln3 activity (Elion et al., Cell 60:649–664, 1990).

Several lines of evidence suggest that mammalian G1 to S transitions may be regulated by similar mechanisms: regulatory molecules (Cdc2 kinases and cyclins) similar to those found in yeast are observed in mammalian G1, and like *S. cerevisiae*, mammalian cells arrest in G1 when deprived of nutrients and in response to certain negative regulatory signals, including contact with other cells or treatment with negative growth factors (e.g., TGF-β) (FIG. 1B). However, several considerations suggest that the higher eukaryotic G1 regulatory machinery is likely to be more sophisticated than that of yeast. First, in mammalian cells there appear to be more proteins involved in the process. At least ten different Cdc2 family proteins and related protein kinases (see Meyerson et al., EMBO J. 11:2909–2917, 1992) and at least three distinct classes of putative G1 cyclins (Koff et al., Cell 66:1217–1228, 1991; Matsushime et al., Cell 65:701–713, 1991; Motokura et al., Nature 339:512–518, 1991; Xiong et al., Cell 65:691–699, 1991) have been identified. Second, unlike yeast, the proliferation of most mammalian cells depends on extracellular protein factors (in particular, positive growth regulatory proteins), deprivation of which leads to arrest in G1. Third, arrest of many cell types during G1 can progress to a state, G0, that may not strictly parallel any phase of the yeast cell cycle.

Because proteins involved in controlling normal cell division decisions in mammals (e.g., humans) are also very likely to play a key role in malignant cell growth, identification and isolation of such proteins facilitate the development of useful cancer diagnostics as well as anti-cancer therapeutics. We now describe (i) a novel system for the identification of proteins which, at some time during their existence, participate in a particular protein-protein interaction; (ii) the use of this system to identify interacting proteins which are key regulators of mammalian cell division; and (iii) one such interacting protein, termed Cdi1, a cell cycle control protein which provides a useful tool for cancer diagnosis and treatment.

SUMMARY OF THE INVENTION

In general, the invention features a method for determining whether a first protein is capable of physically interacting (i.e., directly or indirectly) with a second protein. The method involves: (a) providing a host cell which contains (i) a reporter gene operably linked to a protein binding site; (ii) a first fusion gene which expresses a first fusion protein, the first fusion protein including the first protein covalently bonded to a binding moiety which is capable of specifically binding to the protein binding site; and (iii) a second fusion gene which expresses a second fusion protein, the second fusion protein including the second protein covalently bonded to a weak gene activating moiety; and (b) measuring expression of the reporter gene as a measure of an interaction between the first and the second proteins. In a preferred embodiment, the method further involves isolating the gene encoding the second protein.

In other preferred embodiments, the weak gene activating moiety is of lesser activation potential than GAL4 activation region II and preferably is the gene activating moiety of B42 or a gene activating moiety of lesser activation potential; the host cell is a yeast cell; the reporter gene includes the LEU2 gene or the lacZ gene; the host cell further contains a second reporter gene operably linked to the protein binding site, for example, the host cell includes both a LEU2 reporter gene and a lacZ reporter gene; the protein binding site is a LexA binding site and the binding moiety includes a LexA DNA binding domain; the second protein is a protein involved in the control of eukaryotic cell division, for example, a Cdc2 cell division control protein.

In a second aspect, the invention features a substantially pure preparation of Cdi1 polypeptide. Preferably, the Cdi1 polypeptide includes an amino acid sequence substantially identical to the amino acid sequence shown in FIG. 6 (SEQ ID NO: 1); and is derived from a mammal, for example, a human.

In a related aspect, the invention features purified DNA (for example, cDNA) which includes a sequence encoding a Cdi1 polypeptide, and preferably a human Cdi1 polypeptide, of the invention.

In other related aspects, the invention features a vector and a cell which includes a purified DNA of the invention; a purified antibody which specifically binds a Cdi1 polypeptide of the invention; and a method of producing a recombinant Cdi1 polypeptide involving, providing a cell transformed with DNA encoding a Cdi1 polypeptide positioned for expression in the cell; culturing the transformed cell under conditions for expressing the DNA; and isolating the recombinant Cdi1 polypeptide. The invention further features recombinant Cdi1 polypeptide produced by such expression of a purified DNA of the invention.

In yet another aspect, the invention features a therapeutic composition which includes as an active ingredient a Cdi1 polypeptide of the invention, the active ingredient being formulated in a physiologically-acceptable carrier. Such a therapeutic composition is useful in a method of inhibiting cell proliferation in a mammal, involving administering the therapeutic composition to the mammal in a dosage effective to inhibit mammalian cell division.

In a final aspect, the invention features a method of detecting a malignant cell in a biological sample, involving measuring Cdi1 gene expression in the sample, a change in Cdi1 expression relative to a wild-type sample being indicative of the presence of the malignant cell.

As used herein, by "reporter gene" is meant a gene whose expression may be assayed; such genes include, without limitation, lacZ, amino acid biosynthetic genes, e.g. the yeast LEU2, HIS3, LYS2, or URA3 genes, nucleic acid biosynthetic genes, the mammalian chloramphenicol transacetylase (CAT) gene, or any surface antigen gene for which specific antibodies are available.

By "operably linked" is meant that a gene and a regulatory sequence(s) are connected in such a way as to permit gene expression when the appropriate molecules (e.g., transcriptional activator proteins or proteins which include transcriptional activation domains) are bound to the regulatory sequence(s).

By a "binding moiety" is meant a stretch of amino acids which is capable of directing specific polypeptide binding to a particular DNA sequence (i.e., a "protein binding site").

By "weak gene activating moiety" is meant a stretch of amino acids which is capable of weakly inducing the expression of a gene to whose control region it is bound. As used herein, "weakly" is meant below the level of activation effected by GAL4 activation region II (Ma and Ptashne, Cell 48:847, 1987) and is preferably at or below the level of activation effected by the B42 activation domain of Ma and Ptashne (Cell 51:113, 1987). Levels of activation may be measured Using any downstream reporter gene system and comparing, in parallel assays, the level of expression stimulated by the GAL4 region II-polypeptide with the level of expression stimulated by the polypeptide to be tested.

By "substantially pure" is meant a preparation which is at least 60% by weight (dry weight) the compound of interest, e.g., a Cdi1 polypeptide. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

By "purified DNA" is meant DNA that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By "substantially identical" is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the protein (assayed, e.g., as described herein). A "substantially identical" nucleic acid sequence codes for a substantially identical amino acid sequence as defined above.

By "transformed cell" is meant a cell into which (or into an ancestor of which) has been introduced, by means of recombinant DNA techniques, a DNA molecule encoding (as used herein) a Cdi1 polypeptide.

By "positioned for expression" is meant that the DNA molecule is positioned adjacent to a DNA sequence which directs transcription and translation of the sequence (i.e., facilitates the production of, e.g., a Cdi1 polypeptide).

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody, e.g., Cdi1-specific antibody. A purified Cdi1 antibody may be obtained, for example, by affinity chromatography using recombinantly-produced Cdi1 polypeptide and standard techniques.

By "specifically binds" is meant an antibody which recognizes and binds Cdi1 polypeptide but which does not substantially recognize and bind other molecules in a sample, e.g., a biological sample, which naturally includes Cdi1 polypeptide.

By a "malignant cell" is meant a cell which has been released from normal cell division control. Included in this definition are transformed and immortalized cells.

The interaction trap system described herein provides advantages over more conventional methods for isolating interacting proteins or genes encoding interacting proteins. Most notably, applicants' system provides a rapid and inexpensive method having very general utility for identifying and purifying genes encoding a wide range of useful proteins based on the protein's physical interaction with a polypeptide of known diagnostic or therapeutic usefulness. This general utility derives in part from the fact that the components of the system can be readily modified to facilitate detection of protein interactions of widely varying affinity (e.g., by using reporter genes which differ quantitatively in their sensitivity to a protein interaction). The inducible nature of the promoter used to express the interacting proteins also increases the scope of candidate interactors which may be detected since even proteins whose chronic expression is toxic to the host cell may be isolated simply by inducing a short burst of the protein's expression and testing for its ability to interact and stimulate expression of a β-galactosidase reporter gene.

Moreover, detection of interacting proteins through the use of a weak gene activation domain tag avoids the restrictions on the pool of available candidate interacting proteins which is characteristically associated with stronger activation domains (such as GAL4 or VP16); although the mechanism is unclear, such a restriction apparently results from low to moderate levels of host cell toxicity mediated by the strong activation domain.

Other features and advantages of the invention will be apparent from the following detailed description thereof, and from the claims.

BRIEF DESCRIPTION OF THE DRAWINGS

The drawings are first briefly described.

FIG. 1 illustrates cell cycle control systems.

FIG. 3 illustrates examples of each component of the interaction trap system. FIG. 3A is a diagrammatic representation of a "bait" protein useful in the invention; the numbers represent amino acids. FIG. 3B is a diagrammatic representation of reporter genes useful in the invention. FIG. 3C is a diagrammatic representation of a library expression plasmid useful in the invention and the N-terminal amino acid sequence of an exemplary "prey" protein according to the invention (SEQ ID NO:33).

FIG. 6 shows the Cdi1 coding sequence together with the predicted amino-acid sequence of its open reading frame (SEQ ID NO:1).

FIG. 7 shows the effect of Cdi1 on yeast cell growth.

FIG. 8 shows the morphology of cells that express Cdi1. (A) shows control cells; (B) shows control cells stained with DAPI; (C) shows cells expressing Cdi1; and (D) shows cells expressing Cdi1 stained with DAPI.

FIG. 9 shows Cdi1 expression in HeLa cells. FIG. 9A indicates the timing of expression; lanes represent different timepoints: (1) 0 h, (2) 3 h, (3) 6 h, (4) 9 h, (5) 12 h, (6) 15 h, (7) 18 h, (8) 21 h, (9) 24 h, and (10) 27 h after release. FIG. 9B shows the effect of Cdi1 overexpression.

FIG. 10 shows an alignment of Cdc2 proteins and FUS3. Depicted is an alignment of the sequences of the bait proteins used herein. Amino acids are numbered as in human Cdc2. Abbreviations are as follows: HsCdc2, human Cdc2; HsCdk2, human Cdk2; ScCdc28, *S. cerevisiae* Cdc28; DmCdc2 and DmCdc2c, the two Drosophila Cdc2 isolates; and ScFus3, *S. cerevisiae* FUS3. Residues shown in boldface are conserved between the Cdc2 family members; residues present in Fus3 are also shown in bold. Asterisks indicate potential Cdi1 contact points, i.e., amino acids that are conserved among human Cdc2, Cdk2, *S. cerevisiae* Cdc28, and Drosophila Cdc2, but that differ in Drosophila Cdc2c and in Fus3.

There now follows a description of one example of an interaction trap system and its use for isolating a particular cell division protein. This example is designed to illustrate, not limit, the invention.

DETAILED DESCRIPTION

Applicants have developed an in vivo interaction trap system for the isolation of genes encoding proteins which physically interact with a second protein of known diagnostic or therapeutic utility. The system involves a eukaryotic host strain (e.g., a yeast strain) which is engineered to express the protein of therapeutic or diagnostic interest as a fusion protein covalently bonded to a known DNA binding domain; this protein is referred to as a "bait" protein because its purpose in the system is to "catch" useful, but as yet unknown or uncharacterized, interacting polypeptides (termed the "prey"; see below). The eukaryotic host strain also contains one or more "reporter genes", i.e., genes whose transcription is detected in response to a bait-prey interaction. Bait proteins, via their DNA binding domain, bind to their specific DNA site upstream of a reporter gene; reporter transcription is not stimulated, however, because the bait protein lacks its own activation domain.

To isolate genes encoding novel interacting proteins, cells of this strain (containing a reporter gene and expressing a bait protein) are transformed with individual members of a DNA (e.g., a cDNA) expression library; each member of the library directs the synthesis of a candidate interacting protein fused to a weak and invariant gene activation domain tag. Those library-encoded proteins that physically interact with the promoter-bound bait protein are referred to as "prey" proteins. Such bound prey proteins (via their activation domain tag) detectably activate the transcription of the downstream reporter gene and provide a ready assay for identifying particular cells which harbor a DNA clone encoding an interacting protein of interest.

Figure 1A:
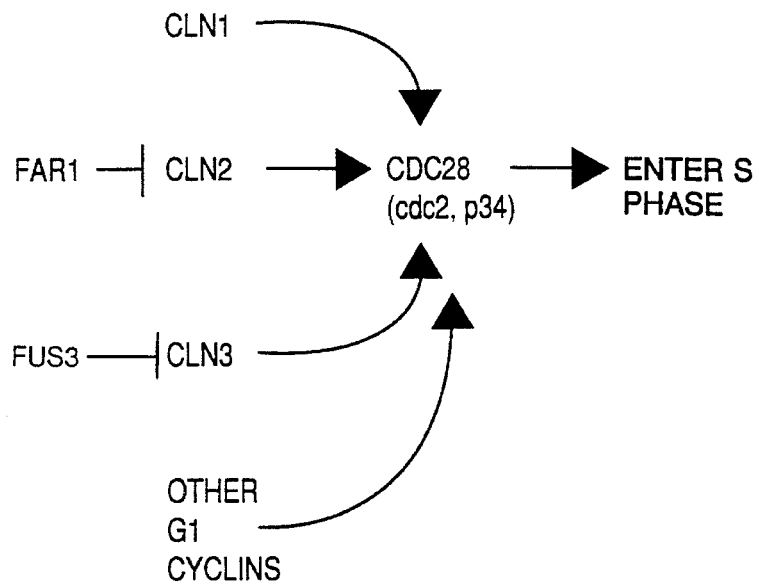
FIG. 1(A) illustrates G1 control in yeast.
Figure 1B:
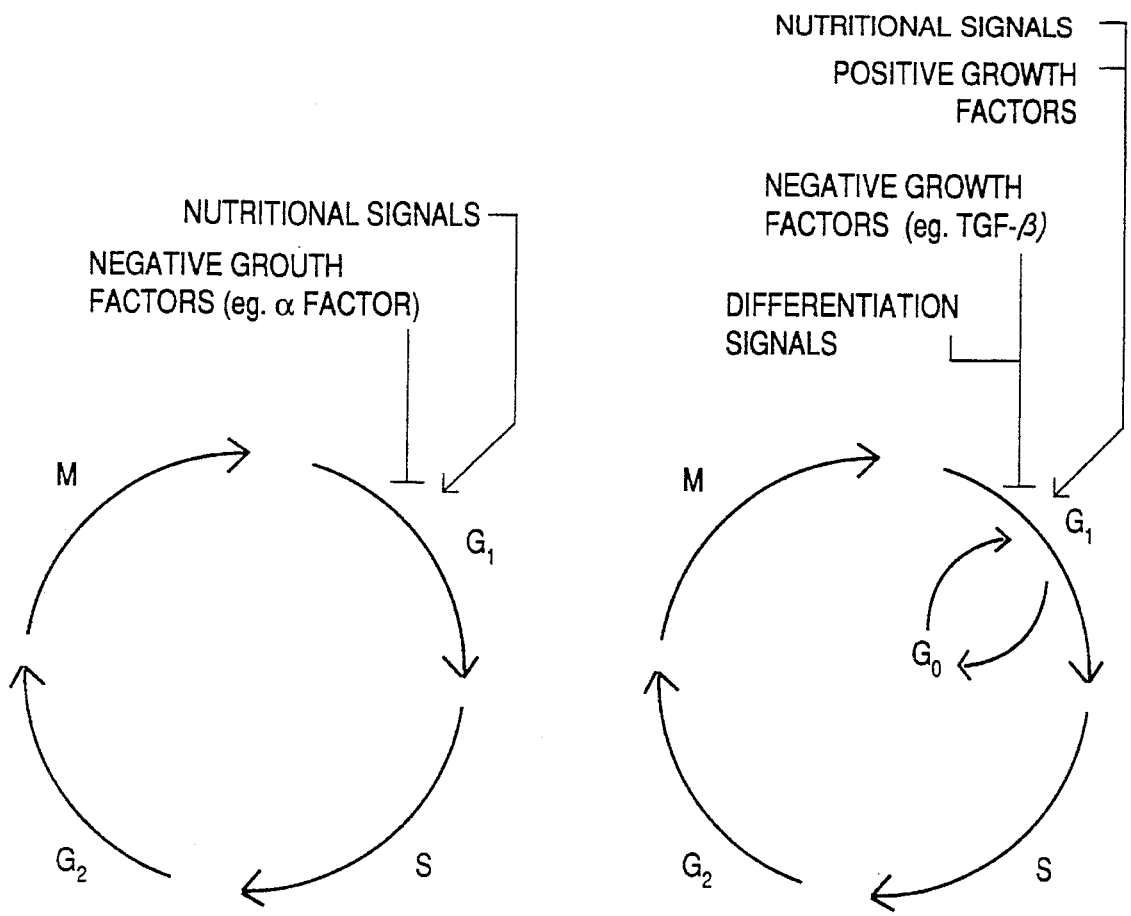
FIG. 1B illustrates cell cycle control in yeast and mammals.
Figure 2A:
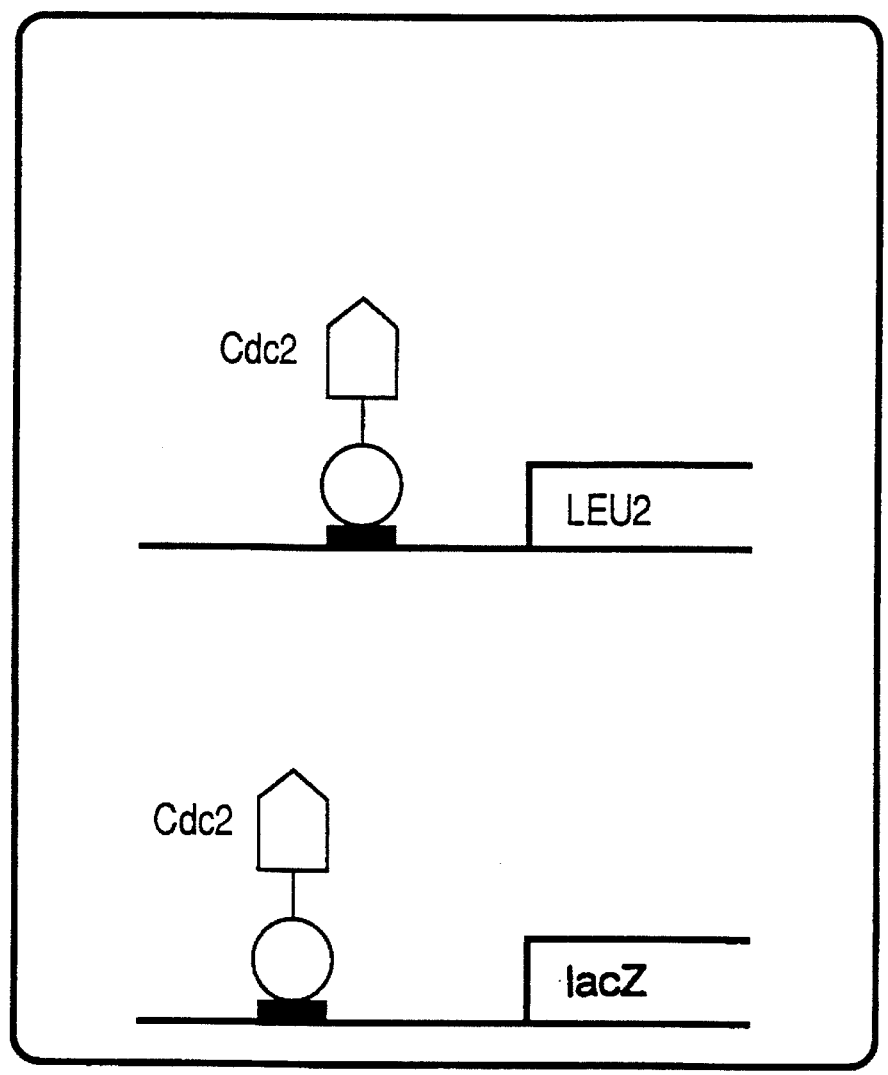
FIG. 2A–C illustrates an interaction trap system according to the invention.
Figure 2B:
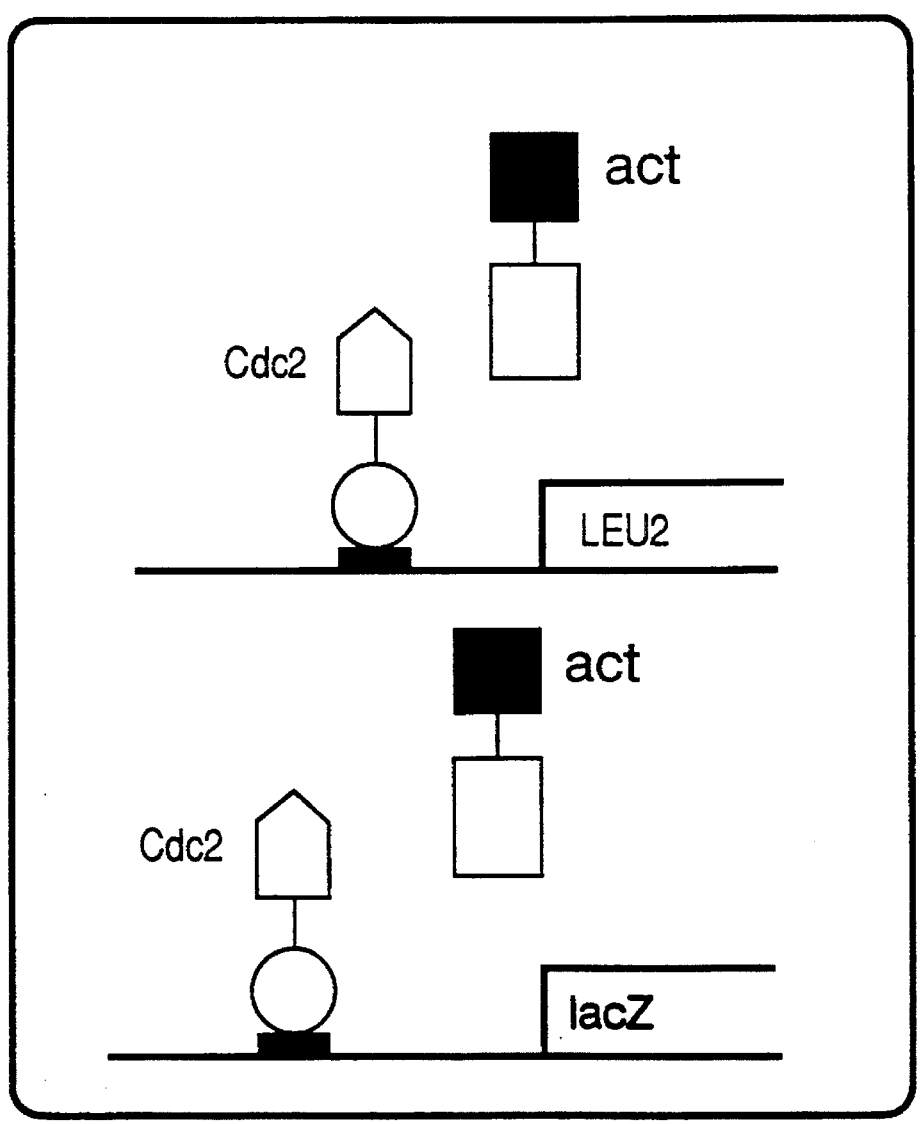
Figure 2C:
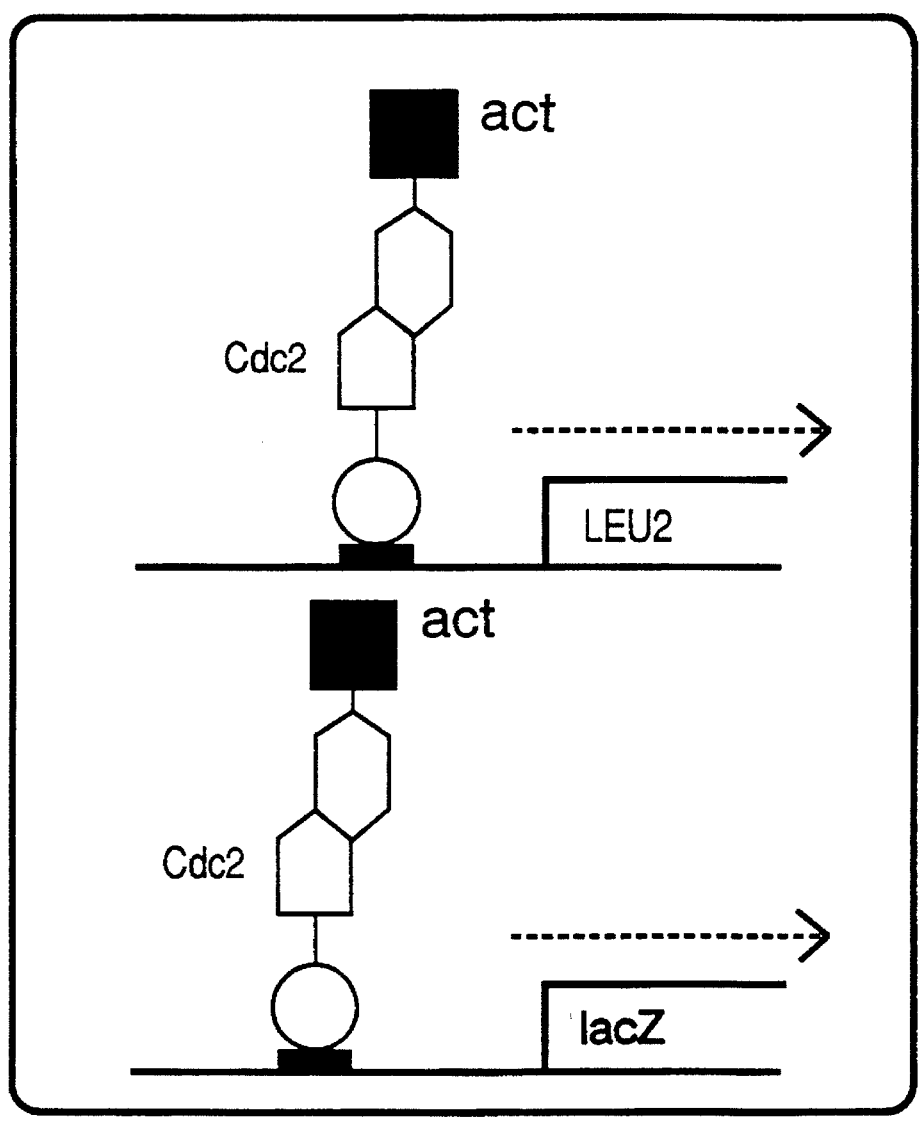

One example of such an interaction trap system is shown in FIG. 2. FIG. 2A shows a yeast strain containing two reporter genes, LexAop-LEU2 and LexAop-lacZ, and a constitutively expressed bait protein, LexA-Cdc2. Synthesis of prey proteins is induced by growing the yeast in the presence of galactose. FIG. 2B shows that if the prey protein does not interact with the transcriptionally-inert LexA-fusion bait protein, the reporter genes are not transcribed; the cell cannot grow into a colony on leu⁻ medium, and it is white on Xgal medium because it contains no β-galactosidase activity. FIG. 2C shows that, if the prey protein interacts with the bait, then both reporter genes are active; the cell forms a colony on leu⁻ medium, and cells in that colony have β-galactosidase activity and are blue on Xgal medium.

As described herein, in developing the interaction trap system shown diagrammatically in FIG. 2, careful attention was paid to three classes of components: (i) use of bait proteins that contained a site-specific DNA binding domain that was known to be transcriptionally inert; (ii) use of reporter genes that had essentially no basal transcription and that were bound by the bait protein; and (iii) use of library-encoded prey proteins, all of which were expressed as chimeras whose amino termini contained the same weak activation domain and, preferably, other useful moieties, such as nuclear localization signals.

Each component of the system is now described in more detail.

Bait proteins

The selection host strain depicted in FIG. 2 contains a Cdc2 bait and a DNA binding moiety derived from the bacterial LexA protein (see FIG. 3A). The use of a LexA DNA binding domain provides certain advantages. For example, in yeast, the LexA moiety contains no activation function and has no known effect on transcription of yeast genes (Brent and Ptashne, Nature 312:612–615, 1984; Brent and Ptashne, Cell 43:729–736, 1985). In addition, use of the LexA rather than the GAL4 DNA-binding domain allows conditional expression of prey proteins in response to galactose induction; this facilitates detection of prey proteins which might be toxic to the host cell if expressed continuously. Finally, the use of LexA allows knowledge regarding the interaction between LexA and the LexA binding site (i.e., the LexA operator) to be exploited for the purpose of optimizing operator occupancy.

The bait protein illustrated in FIG. 3A also includes a LexA dimerization domain; this optional domain facilitates efficient LexA dimer formation. Because LexA binds its DNA binding site as a dimer, inclusion of this domain in the bait protein also optimizes the efficiency of operator occupancy (Golemis and Brent, Mol. Cell Biol. 12:3006–3014, 1992).

LexA represents a preferred DNA binding domain in the invention. However, any other transcriptionally-inert or essentially transcriptionally-inert DNA binding domain may be used in the interaction trap system; such DNA binding domains are well known and include the DNA binding portions of the proteins ACE1 (CUP1), lambda cI, lac repressor, jun fos, or GCN4. For the above-described reasons, the GAL4 DNA binding domain represents a slightly less preferred DNA binding moiety for the bait proteins.

Bait proteins may be chosen from any protein of known or suspected diagnostic or therapeutic importance. Preferred bait proteins include oncoproteins (such as myc, particularly the C-terminus of myc, ras, src, fos, and particularly the oligomeric interaction domains of fos) or any other proteins involved in cell cycle regulation (such as kinases, phosphatases, the cytoplasmic portions of membrane-associated receptors, and other Cdc2 family members). In each case, the protein of diagnostic or therapeutic importance would be fused to a known DNA binding domain as generally described for LexA-Cdc2.

Reporters

As shown in FIG. 3B, one preferred host strain according to the invention contains two different reporter genes, the LEU2 gene and the lacZ gene, each carrying an upstream binding site for the bait protein. The reporter genes depicted in FIG. 3B each include, as an upstream binding site, one or more LexA operators in place of their native Upstream Activation Sequences (UASs). These reporter genes may be integrated into the chromosome or may be carried on autonomously replicating plasmids (e.g., yeast 2μ plasmids).

A combination of two such reporters is preferred in the invention for a number of reasons. First, the LexAop-LEU2 construction allows cells that contain interacting proteins to select themselves by growth on medium that lacks leucine, facilitating the examination of large numbers of potential interactor protein-containing cells. Second, the LexAop-lacZ reporter allows LEU⁺ cells to be quickly screened to confirm an interaction. And, third, among other technical considerations (see below), the LexAop-LEU2 reporter provides an extremely sensitive first selection, while the Lex-Aop-lacZ reporter allows discrimination between proteins of different interaction affinities.

Although the reporter genes described herein represent a preferred embodiment of the invention, other equivalent genes whose expression may be detected or assayed by standard techniques may also be employed in conjunction with, or instead of, the LEU2 and lacZ genes. Examples of other useful genes whose transcription can be detected include amino acid and nucleic acid biosynthetic genes (such as yeast HIS3, URA3, and LYS2) GAL1, E. coli galK (which complements the yeast GAL1 gene), and the higher cell reporter genes CAT, GUS, and any gene encoding a cell surface antigen for which antibodies are available (e.g., CD4).

Prey proteins

In the selection described herein, a fourth DNA construction was utilized which encoded a series of candidate interacting proteins, each fused to a weak activation domain (i.e., prey proteins). One such prey protein construct is shown in FIG. 3C; this plasmid encodes a prey fusion protein which includes an invariant N-terminal moiety. This moiety carries, amino to carboxy terminal, an ATG for protein expression, an optional nuclear localization sequence, a weak activation domain (i.e., the B42 activation domain of Ma and Ptashne; Cell 51:113, 1987), and an optional epitope tag for rapid immunological detection of fusion protein synthesis. As described herein, a HeLa cDNA library was constructed, and random library sequences were inserted downstream of this N-terminal fragment to produce fusion genes encoding prey proteins.

Prey proteins other than those described herein are also useful in the invention. For example, cDNAs may be constructed from any mRNA population and inserted into an equivalent expression vector. Such a library of choice may be constructed de novo using commercially available kits (e.g., from Stratagene, La Jolla, Calif.) or using well established preparative procedures (see, e.g., *Current Protocols in Molecular Biology*, New York, John Wiley & Sons, 1987). Alternatively, a number of cDNA libraries (from a number of different organisms) are publically and commercially available; sources of libraries include, e.g., Clontech (Palo Alto, Calif.) and Stratagene (La Jolla, Calif.). It is also noted that prey proteins need not be naturally occurring full length polypeptides. For example, a prey protein may be encoded by a synthetic sequence or may be the product of a randomly generated open reading frame or a portion thereof. In one particular example, the prey protein includes only an interaction domain; such a domain may be useful as a therapeutic to modulate bait protein activity.

Similarly, other weak activation domains may be substituted for the B42 portion of the prey molecule; such activation domains must be weaker than the GAL4 activation region II moiety and preferably should be no stronger than B42 (as measured, e.g., by a comparison with GAL4 activation region II or B42 in parallel β-galactosidase assays using lacZ reporter genes); such a domain may, however, be weaker than B42. In particular, the extraordinary sensitivity of the LEU2 selection scheme (described above) allows even extremely weak activation domains to be utilized in the invention. Examples of other useful weak activation domains include B17, B112, and the amphipathic helix (AH) domains described in Ma and Ptashne (Cell 51:113, 1987), Ruden et al. (Nature 350:426–430, 1991), and Giniger and Ptashne (Nature 330:670, 1987).

Finally, the prey proteins, if desired, may include other optional nuclear localization sequences (e.g., those derived from the GAL4 or MATα2 genes) or other optional epitope tags (e.g., portions of the c-myc protein or the flag epitope available from Immunex). These sequences optimize the efficiency of the system, but are not absolutely required for its operation. In particular, the nuclear localization sequence optimizes the efficiency with which prey molecules reach the nuclear-localized reporter gene construct(s), thus increasing their effective concentration and allowing one to detect weaker protein interactions; and the epitope tag merely facilitates a simple immunoassay for fusion protein expression.

Those skilled in the art will also recognize that the above-described reporter gene, DNA binding domain, and gene activation domain components may be derived from any appropriate eukaryotic or prokaryotic source, including yeast, mammalian cell, and prokaryotic cell genomes or cDNAs as well as artificial sequences. Moreover, although yeast represents a preferred host organism for the interaction trap system (for reasons of ease of propagation, genetic manipulation, and large scale screening), other host organisms such as mammalian cells may also be utilized. If a mammalian system is chosen, a preferred reporter gene is the sensitive and easily assayed CAT gene; useful DNA binding domains and gene activation domains may be chosen from those described above (e.g., the LexA DNA binding domain and the B42 or B112 activation domains).

The general type of interaction trap system described herein provides a number of advantages. For example, the system can be used to detect bait-prey interactions of varying affinity. This can be accomplished, e.g., by using reporter genes which differ quantitatively in their sensitivity to an interaction with a library protein. In particular, the equilibrium Kd with which a library-encoded protein must interact with the bait to activate the LexAop-LEU2 reporter is probably $\leq 10^{-6}$M. This value is clearly sufficient to detect protein interactions that are weaker and shorter lived than those detected, e.g., by typical physical methods. The lacZ reporters are less sensitive, allowing the selection of different prey proteins by utilizing reporters with the appropriate number, affinity, and position of LexA operators; in particular, sensitivity of the lacZ reporter gene is increased by either increasing the number of upstream LexA operators, utilizing LexA operators which have increased affinity for LexA binding dimers, and/or decreasing the distance between the LexA operator and the downstream reporter gene promoter. This ability to manipulate the sensitivity of the system provides a measure of control over the strength of the interactions detected and thus increases the range of proteins which may be isolated.

The system provides at least three other advantages. First, the activation region on the library-encoded proteins is relatively weak, in order to avoid restrictions on the spectrum of library proteins detected; such restrictions are common when utilizing a strong, semi-toxic activation domain such as that of GAL4 or VP16 (Gill and Ptashne, Nature 334:721–724, 1988; Triezenberg et al., Genes Dev. 2:730–742, 1988; Berger et al., Cell 70:251–265, 1992). Second, the use of LexA to bind the bait to DNA allows the use of GAL4$^+$ yeast hosts and the use of the GAL1 promoter to effect conditional expression of the library protein. This in turn allows the Leu or lacZ phenotypes to be unconditionally ascribed to expression of the library protein and minimizes the number of false positives; it also allows conditional expression and selection of interactor proteins which are toxic to the host cell if continuously produced. And third, placing the activation domain at the amino terminus, rather than at the carboxy terminus, of the fusion protein guarantees that the activation domain portion of the protein will be translated in frame, and therefore that one out of three fusion genes will encode a candidate activation domain-tagged interactor protein.

One particular interaction trap system is now described. The use of this system to isolate a protein (termed Cdi1) which physically interacts with a known cell division control protein (termed Cdc2) is also illustrated.

Isolation and Characterization of Cdi1

Isolation of the Cdi1 cDNA

To isolate proteins which interact with the cell division control protein Cdc2, the yeast strain EGY48/p1840 was utilized. This strain contained both the LexAop-LEU2 and LexAop-lacZ reporters, as well as a plasmid that directed the synthesis of a LexA-Cdc2 bait protein (see below). The LexAop-LEU2 reporter replaced the chromosomal LEU2 gene. This reporter carried 3 copies of the high affinity colE1 double LexA operator (Ebina et al., J. Biol. Chem. 258:13258–13261, 1983) 40 nucleotides upstream of the major LEU2 transcription startpoint. The LexAop-lacZ reporter (p1840) was carried on a URA3$^+$ 2µ plasmid. This reporter carried a single LexA operator 167 nucleotides upstream of the major GAL1 transcription startpoint.

A HeLa cDNA interaction library (described below) was also introduced into this strain using the plasmid depicted in FIG. 3C (termed pJG4-5); this library vector was designed to direct the conditional expression of proteins under the control of a derivative of the GAL1 promoter. This plasmid carried a 2µ replicator and a TRP1$^+$ selectable marker. cDNA was inserted into this plasmid on EcoR1-XhoI fragments. Downstream of the XhoI site, pJG4-5 contained the ADH1 transcription terminator. The sequence of an invariant 107 amino acid moiety, encoded by the plasmid and fused to the N-terminus of all library proteins, is shown below the plasmid map in FIG. 3C. This moiety carries, amino to carboxy terminal, an ATG, the SV40 T nuclear localization sequence (Kalderon et al., Cell 39:499–509, 1984), the B42 transcription activation domain, (Ma and Ptashne, Cell 51:113–119, 1987; Ruden et al., Nature 350:426–430, 1991) and the 12CA5 epitope tag from the influenza virus hemagglutinin protein (Green et al., Cell 28:477–487, 1982).

Following introduction of the prey-encoding plasmids into EGY48/p1840, over a million transformants were isolated, of which 3–4×10$^5$ expressed fusion proteins (see experimental procedures below). The colonies were pooled, diluted, and grown for five hours in liquid culture in the presence of galactose to induce synthesis of library-encoded proteins. The pool was then diluted again so that each original transformant was represented about 20 times and plated on galactose-containing medium without leucine. From about 2×10$^7$ cells, 412 LEU2$^+$ colonies were isolated. of these colonies were blue on galactose Xgal medium, presumably due to the lower sensitivity of the lacZ reporter. In all cells in which both reporters were active, both phenotypes were galactose-dependent, confirming that they required the library-encoded protein. Library plasmids were rescued from these cells, assigned to one of three classes by restriction mapping, and the plasmids identified from each class that contained the longest cDNA inserts. Synthesis of a fusion protein by the plasmid was verified in each case by Western blot analysis using anti-epitope antiserum.

Further analysis by detailed mapping and partial DNA sequencing showed that two of the recovered cDNA classes were identical to previously identified genes encoding CKS1hs and CKS2hs (Richardson et al., Genes Dev. 4:1332–1344, 1990), human homologs of the *S. pombe* suc1$^+$ product. Sequencing of the third restriction map class showed it to be a previously unidentified gene. This gene was termed CDI1, for Cdc2 Interactor 1; its protein product was termed Cdi1.

Figure 4:
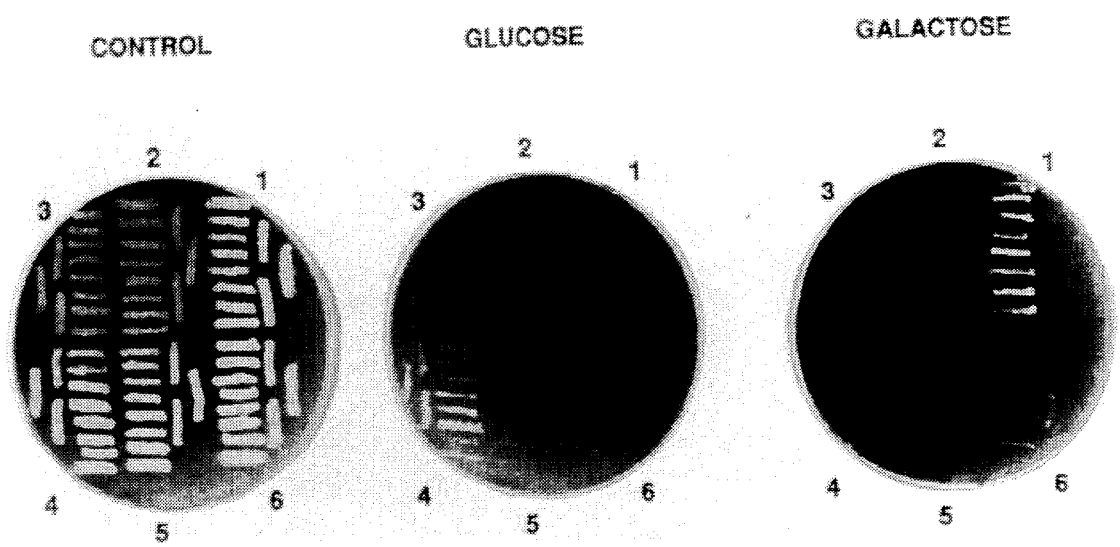
FIG. 4 depicts yeast assays demonstrating the specificity of the Cdi1/Cdc2 interaction.

The CDI1 gene was introduced into a panel of EGY48-derived strains (i.e., EGY48/1840 containing different LexA fusion baits) in order to test the reproducibility and specificity of the interaction between Cdc2 and Cdi1. Cells from 8 individual transformed cells that contained Cdi1 plus a given bait (horizontal streaks) or the same bait plus the library vector as a control (adjacent vertical streaks) were streaked with toothpicks onto each of three plates (FIG. 4). The plates, shown in FIG. 4, included a "control" plate, a Ura$^-$ Trp$^-$ His$^-$ glucose plate which selected for the presence of the bait plasmid, the LexAop-lacZ reporter, and the Cdi1 expression plasmid; a "glucose" plate, a Ura$^-$ Trp$^-$ His$^-$ Leu$^-$ glucose plate, which additionally selected for activation of the LexAop-LEU2 reporter; and a "galactose" plate, a Ura$^-$ Trp$^-$ His$^-$ Leu$^-$ galactose plate, which selected for the activation of the LexAop-LEU2 reporter, and which induced the expression of Cdi1. Baits used in this test included: (1) LexA-Cdc2, (2) LexA-Bicoid, (3) LexA-Max, (4) LexA-Cln3, (5) LexA-Fus3, and (6) LexA-cMyc-Cterm (FIG. 4).

As judged by the LEU2 and lacZ transcription phenotypes, Cdi1 interacted specifically with LexA-Cdc2, and did not interact with LexA-cMyc-Cterm, LexA-Max, LexA-Bicoid, LexA-Cln3, or LeyA-Fus3 (FIG. 4). Cdi1 also interacted with other Cdc2 family proteins, including LexA-Cdc28, as discussed below. Applicants also note that, on glucose, the LexA-Cln3 bait weakly activated the LexAop-LEU2 reporter, but that, on galactose, the inferiority of the carbon source and the dimished bait expression from the ADH1 promoter eliminated this background.

The specificity of the Cdi1/Cdc2 interaction was then confirmed by physical criteria, in particular, by immunoprecipitation experiments. Extracts were made from EGY48 cells that contained a library plasmid that directed the synthesis of tagged Cdi1 and that also contained either a LexA-Cdc2 or a LexA-Bicoid bait.

In particular, 100 ml of cells were grown in glucose or galactose medium (in which Cdi1 expression was induced) to an OD$_{600}$ of 0.6–0.8, pelleted by centrifugation, resuspended in 500 μl RIPA, lysed by beating with glass beads five times for two minutes each, and spun twice for five minutes in a microfuge (10,000×G) at 4° to remove the beads and cell debris. 5 μl of this supernatant was taken as a control, and 15 μl of rabbit anti-LexA antiserum was added to the remainder, which was incubated at 4° C. for four hours on a rotating platform. LexA-containing proteins were first precipitated from this remainder with 50 μl Staph A-coated sepharose beads (Pharmacia, Piscataway, N.J.) as described in Wittenberg and Reed (Cell 54:1061–1072, 1988). The entire pellet was then dissolved in Laemmli sample buffer, run on a 12.5% protein gel (SDS/PAGE), and blotted onto nitrocellulose. Tagged Cdi1 fusion proteins were identified by Western analysis of the blotted proteins with the 12CA5 monoclonal antihemagglutinin antibody essentially as described in Samson et al. (Cell 57:1045–1052, 1989).

Figure 5:
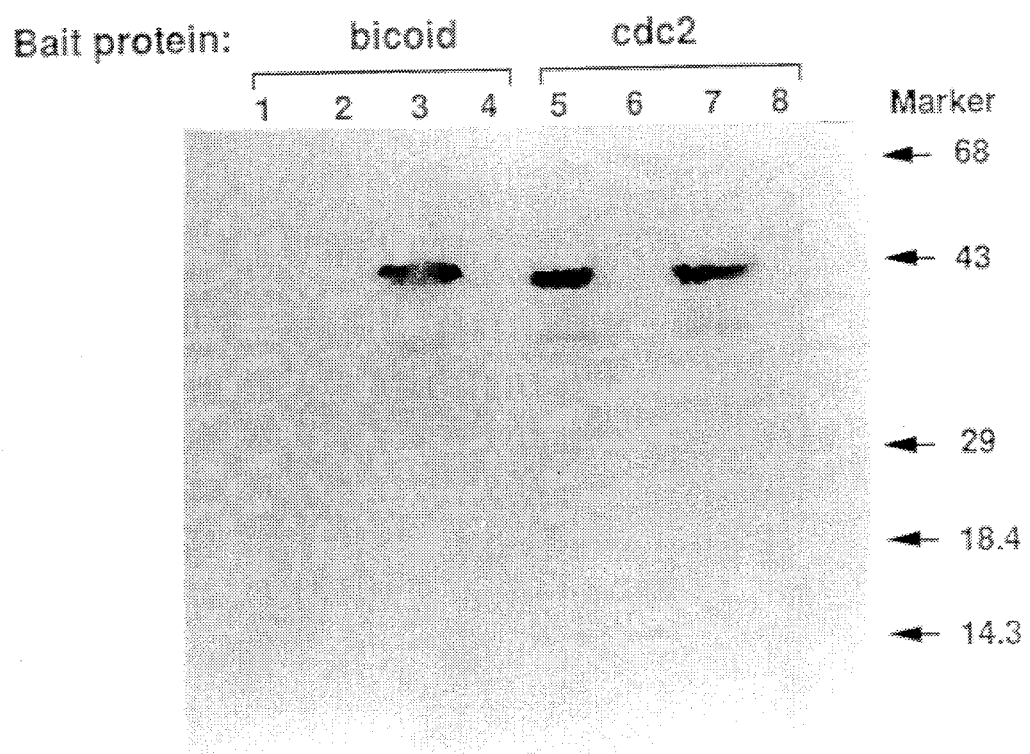
FIG. 5 shows the results of an immunoprecipitation experiment demonstrating that Cdi1 physically interacts with Cdc2.

The results are shown in FIG. 5; the lanes are as follows: (1) Galactose medium, LexA-Bicoid bait, immunoprecipitation; (2) Glucose medium, LexA-Bicoid bait, immunoprecipitation; (3) Galactose medium, LexA-Bicoid bait, cell extract; (4) Glucose medium, LexA-Bicoid bait, cell extract; (5) Galactose medium, LexA-Cdc2 bait, immunoprecipitation; (6) Glucose medium, LexA-Cdc2 bait, immunoprecipitation; (7) Galactose medium, LexA-Cdc2 bait, cell extract; and (8) Glucose medium, LexA-Cdc2 bait, cell extract. As shown in FIG. 5, anti-LexA antiserum precipitated Cdi1 from a yeast extract that contained LexA-Cdc2 and Cdi1, but not from one that contained LexA-Bicoid and Cdi1, thus confirming that Cdi1 physically interacted only with the Cdc2-containing bait protein.

The Cdi1 Protein Product

To analyze the Cdi1 protein product, the Cdi1 cDNA was isolated from 12 different library plasmids that contained cDNAs of 4 different lengths. Sequence analysis revealed that all of the cDNA inserts contained an open reading frame, and inspection of the sequence of the longest cDNAs (FIG. 6) revealed an ATG with a perfect match to the Kozak consensus translation initiation sequence (PuCC/GATGG) (Kozak, Cell 44:283–292, 1986). Careful analysis of the size of the Cdi1 mRNA in HeLa cells revealed that this ATG occurred between 15 and 45 nucleotides from the 5' end of the Cdi1 message, suggesting that the longest cDNAs spanned the entire open reading frame.

The Cdi1 gene is predicted to encode a protein of 212 amino acids. The Cdi1 amino acid sequence does not reveal compelling similarities to any previously identified proteins (FIG. 6). However, two facts about the protein sequence are worth noting. First, 19 of the amino-terminal 35 amino acids are either proline, glutamic acid, serine, or threonine. Proteins that contain these stretches, called PEST sequences, are thought to be degraded rapidly (Rogers et al., Science 234:364–368, 1986); in fact, this stretch of Cdi1 is more enriched in these amino acids than the C-termini of the yeast G1 cyclins, in which the PEST sequences are known to be functional (Cross, Mol. Cell. Biol 8:4675–4684, 1988; Nash et al., EMBO J. 7:4335–4346, 1988; Hadwiger et al., Proc. Nat. Acad. Sci. U.S.A. 86:6255–6259, 1989). Second, since the cDNA library from which the plasmids that encoded Cdi1 were isolated was primed with oligo dT, and since all isolated Cdi1 cDNAs by definition encoded proteins that interacted with Cdc2, analysis of the sizes of Cdi1 cDNA inserts obtained in the screen necessarily localized the portion of the protein sufficient for interaction with Cdc2 to Cdi1's C-terminal ≅170 amino acids.

Analysis Of Cdi1 Function in Yeast

In initial efforts to understand Cdi1 function, the effects of Cdi1 expression in yeast were examined. In particular, because Cdi1 interacts with Cdc2 family proteins, including *S. cerevisiae* Cdc28, an examination of whether Cdi1 affected phenotypes that depended on other known proteins that interact with Cdc28 was undertaken.

Toward this end, the fact that expression of the *S. pombe* suc1$^+$ or *S. cerevisiae* Cks proteins can rescue the temperature sensitivity of strains that bear certain cdc28$^{ts}$ alleles was exploited; this effect is thought to be due to the ability of these proteins to form complexes with the labile Cdc28$^{ts}$ protein, protecting it against thermal denaturation (Hadwiger et al., Proc. Nat. Acad. Sci. U.S.A. 86:6255–6259, 1989). It was found that Cdi1 expression did not rescue the temperature-sensitivity of any cdc28 allele tested, although human Cks2 did.

Next, the ability of Cdi1 to confer on yeast either of two phenotypes associated with expression of *S. cerevisiae* or higher eukaryotic cyclins was examined; such phenotypes include resistance to the arrest of MATa strains by α factor, and rescue of growth arrest of a strain deficient in Cln1, Cln2, and Cln3. Again, however, Cdi1 expression did not confer either phenotype.

Figure 7A:
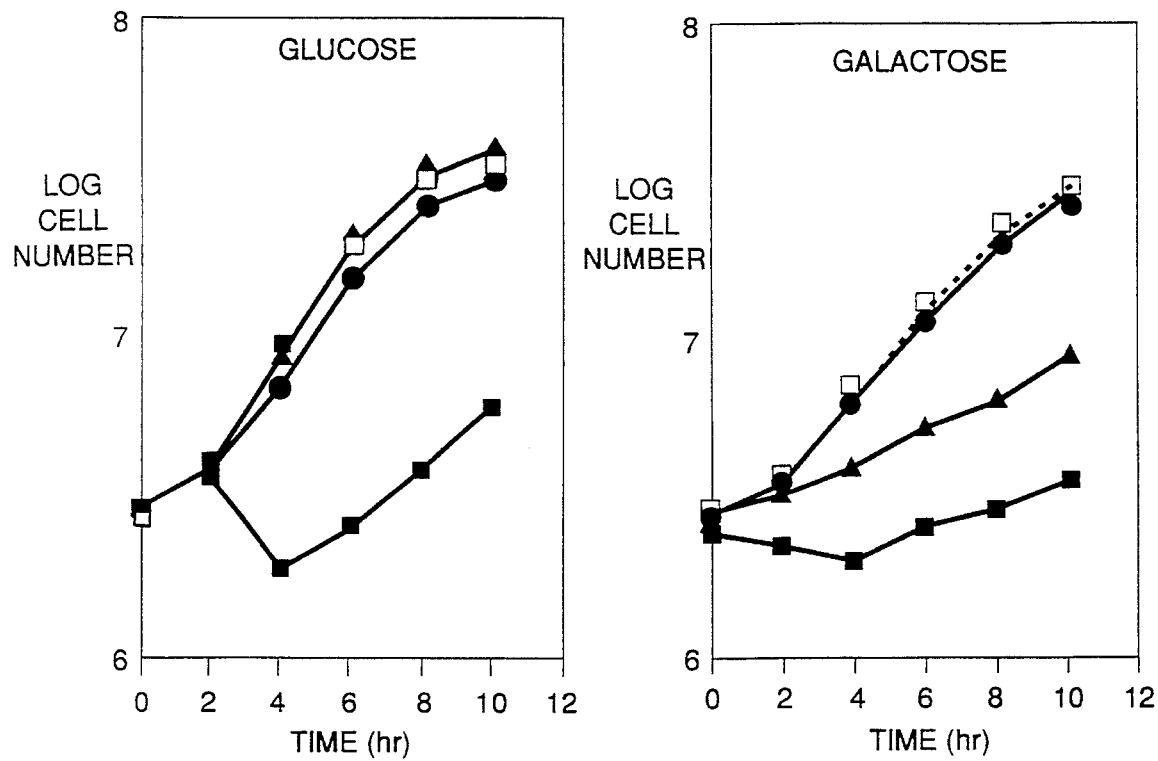
In FIG. 7A, the growth rates of cells that express Cdi1 are depicted; open squares are cells transformed with expression vectors only; ovals are cells expressing Cdc2; triangles are cells expressing Cdi1; and filled squares are cells expressing Cdi1 and Cdc2.

During initial studies, it was noted that expression of Cdi1 inhibited yeast cell cycle progression. Cultures of cells that expressed Cdi1 increased their cell number and optical density more slowly than control populations (FIG. 7A).

To further investigate this growth retardation phenotype, the morphology of Cdi1-expressing cells was examined. W303 cells were transformed with pJG4-4Cdi1, a galactose-inducible vector that directs the synthesis of Cdi1. Morphology of cells was examined with Nomarski optics at 1000× magnification. As shown in FIG. 8, such microscopic examination of the cells showed that, compared with controls, cells in which Cdi1 was expressed were larger, and a subpopulation showed aberrant morphologies: 5% of the cells formed elongated schmoos, and 5% exhibited multiple buds. Immunofluorescent examination of a sample of these cells which had been DAPI stained (as described below) showed that the nuclei of some of the largest cells were not condensed.

Figure 7B:
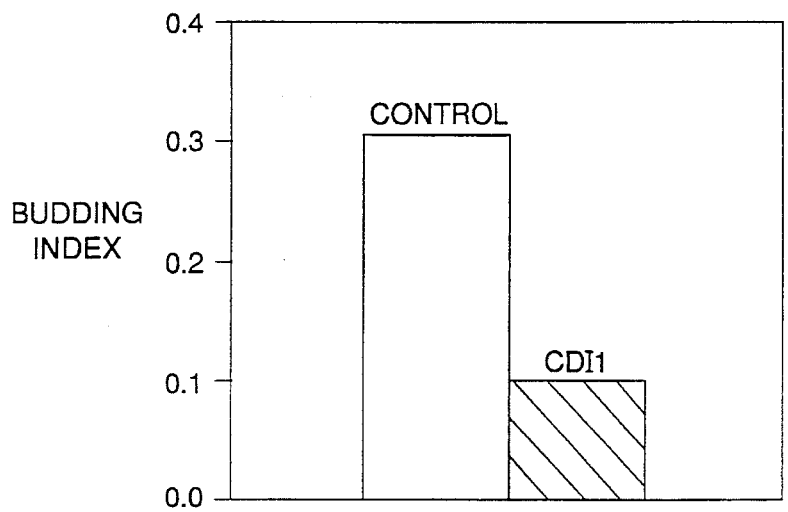
In FIG. 7B is shown a budding index of yeast that express Cdi1.

Finally, cells were examined for their ability to bud. Samples of 400 cells from control populations and from populations expressing Cdi1 were examined by phase contrast microscopy, and the budding index was calculated as the percentage of budded cells in each population as described in Wittenberg and Reed (Mol. Cell. Biol. 9:4064–4068, 1989). As shown in FIG. 7B, less than 10% of the cells in the Cdi1-expressing population showed buds, as opposed to 30% of the cells in the control population, suggesting that fewer of the cells in the population expressing Cdi1 had passed through the G1 to S transition. This finding is consistent with the idea that the increased cell size and growth retardation were also due to a prolongation of G1.

Figure 7C:
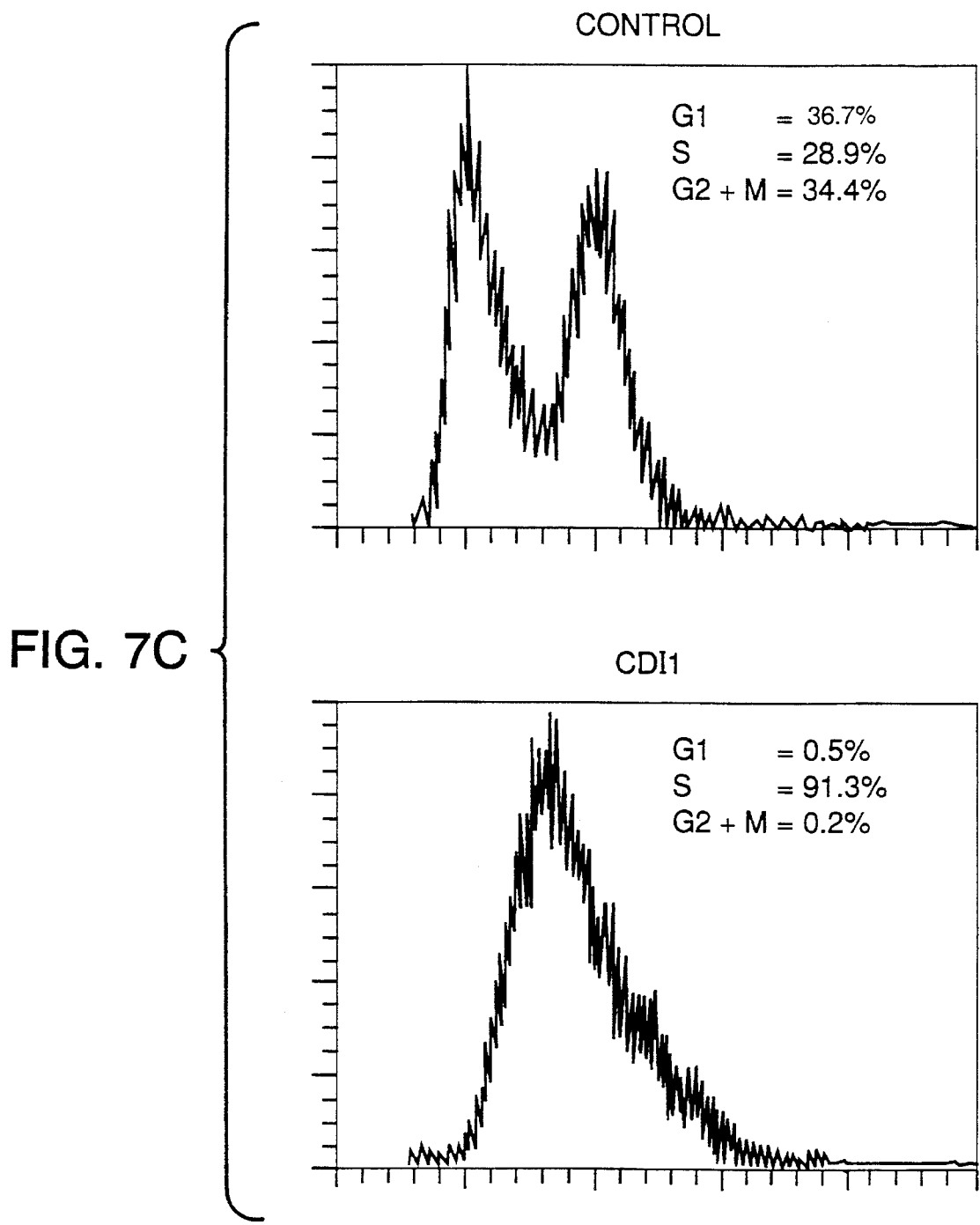
In FIG. 7C is shown a FACS analysis of yeast that express Cdi1; fluorescence (on the x-axis) is shown as a function of cell number (on the Y-axis).

This hypothesis was further tested by FACS analysis of cellular DNA. In particular, W303 cells that contained Cdi1 were grown as described above and diluted to $OD_{600}$=0.1 in 2% glucose or 1% raffinose, 1% galactose, and grown to $OD_{600}$=0.8–1.0. At this point, the cells were collected, sonicated, fixed in 70% ethanol, stained with propidium iodide, and subjected to FACS analysis to determine DNA content as previously described (Lew et al. Cell 63:317–328, 1992). Approximately 20,000 events were analyzed. These results, shown in FIG. 7C, indicated that the majority of the cells in the Cdi1-expressing population had increased amounts of cellular DNA. This may indicate that an increased number of cells were in S phase; alternatively, it may simply be the result of larger cell size and increased quantity of mitochondrial DNA.

Taken together, these experiments thus indicated that protracted Cdi1 expression in *S. cerevisiae* caused a retardation in the passage of cells through the cell cycle, most likely by increasing the proportion of cells in G1; they thus also indicate that Cdi1 expression uncoupled the normal synchrony between these two metrics of cell cycle progression.

Because Cdi1 interacts with Cdc2 family proteins, it was postulated that the Cdi1 growth retardation phenotype in *S. cerevisiae* might be explained by sequestration of Cdc28 into protein complexes that were not competent to cause the cell to traverse G1. To test this hypothesis, the effect of native Cdi1 expression in cells containing Cdc28 with and without overexpressed native human Cdc2 was compared. Specifically, W303 cells that carried the indicated combinations of galactose-inducible Cdi1 expression vector and/or Cdc2 expression vector were grown for 14 h in complete minimal medium lacking tryptophan and histidine in the presence of 2% raffinose. Cells were then washed and diluted to $OD_{600}$=0.1 in the same media containing either 2% glucose, or 1% raffinose and 1% galactose. Optical densities were measured at two hour intervals for 12 hours. The results of these growth assay experiments are shown in FIG. 7A.

Unexpectedly, it was found that the presence of additional Cdc2 increased the severity of the Cdi1-dependent growth inhibition (FIG. 7A). This result suggested that Cdi1 endowed Cdc2 family proteins with a new function, at least in *S. cerevisiae*, one that inhibited their ability to cause cells to traverse G1 and S. The Cdi1 and Cdc2 expression plasmids together also caused some growth inhibition, even in glucose medium; this result was attributed to leaky expression from the GAL1 promoter on the expression plasmid.

Analysis of Cdi1 Function in Mammalian Cells

The above results in yeast suggested that Cdi1 might have a similar effect on the ability of mammalian cells to traverse G1 or S. Since Cdi1 was isolated from HeLa cDNA, the point in the cell cycle at which Cdi1 mRNA was expressed in these cells was first measured.

Specifically, adherent HeLa cells were synchronized in late G1 by a double thymidine block (Rao and Johnson, Nature 225:159–164, 1970) as described in Lew et al. (Cell 66:1197–1206, 1991). Aliquots of cells were collected every three hours after release from the block. Released cells reentered the cell cycle 9 hours after release, as measured by FACS analysis of DNA content. Total RNA was prepared from each aliquot at different time points, run out on a formaldehyde agarose gel, and blotted onto nylon (Nytran, Schleider and Schuell, Keene, N.H.) as described in Ausubel et al. (*Current Protocols in Molecular Biology*, New York, John Wiley & Sons, 1987). The blot was probed with random primed DNA probes (Feinberg and Vogelstein, Anal. Biochem. 132:6–13, 1983) made from a 690 bp EcoRI fragment that contained Cdi1, a 1389 bp PstI fragment from of human cyclin E sequence (Lew et al., Cell 66:1197–1206, 1991), a 1228 bp NcoI-SphI fragment from the coding sequence of the human Cyclin B1 gene (Pines and Hunder, Cell 58:833–846, 1989), and a 1268 bp PstI fragment carrying the full length human glyceraldehyde-phosphate-dehydrogenase (GAPD) gene (Tokunaga et al., Cancer Res. 47:5616–5619, 1987) which served as a normalization control. As is shown in FIG. 9A, expression of Cdi1 mRNA peaks at the end of G1, immediately before the G1 to S transition, in parallel with the expression of the cyclin E message. This temporal expression pattern was consistent with the hypothesis that Cdi1 expression might affect the G1 to S transition.

To further test this idea, HeLa cells were transfected either with pBNCdi1, a construction that directed the synthesis of Cdi1 under the control of the Moloney Murine Leukemia Virus LTR (see below), or with the vector alone. Individual transformed clones were selected by their resistance to G418, and cells from these clones were stained with propidium-iodide and subjected to FACS analysis to determine DNA content (as described below). The midpoint of G1 was defined as the mode of the distribution of each graph; the modes on the two panels were of different heights (272 counts for cells transformed with the vector, 101 counts for cells that contained Cdi1); this broadened peak in the Cdi1-expressing cells reflected the increased proportion of the population that contains approximately 1× DNA content. 4 independent transfectants were analysed; all yielded similar results. These results, which are shown in FIG. 9B, indicated that the populations of cells in which Cdi1 was expressed contained an increased proportion of cells in G1 relative to control populations.

Cdc2-Cdi1 Interaction

To identify determinants of Cdc2 recognized by Cdi1, Cdi1 was tested for its ability to interact with a panel of different bait proteins that included Cdc2 proteins from yeast, humans, and flies, as well as the yeast Fus3 protein kinase (a protein kinase of the ERK class which negatively regulates Cln3 and which, by sequence criteria, is less related to the Cdc2 proteins than those proteins are to one another (Elion et al., Cell 60:649–664, 1990).

To perform these experiments, EGY48/JK103 (described below) containing a plasmid that directed the galactose-inducible synthesis of tagged Cdi1 was transformed with one of a series of different transcriptionally-inert LexA-Cdc2 family protein baits. Five individual transformants of each bait were grown to $OD_{600}$=0.5–1.0 in minimal medium that contained 2% galactose but that lacked uracil, histidine, and tryptophan. Results are shown in Table 1 and are given in β-galactosidase units; variation among individual transformants was less than 20%.

TABLE 1

| Bait | β-Galactosidase Activity |
| --- | --- |
| LexA-Cdc2 (Hs) | 1580 |
| LexA-Cdk2 (Hs) | 440 |
| LexA-Cdc28 (Sc) | 480 |
| LexA-Cdc2 (Dm) | 40 |
| LexA-Cdc2c (Dm) | >2 |
| LexA-Fus3 (Sc) | >2 |

As shown in Table 1, tagged Cdi1 stimulated transcription from these baits to different levels; it activated strongly in strains that contained the human Cdc2 bait, against which it was selected, less strongly in strains that contained S. cerevisiae Cdc28 or human Cdk2 baits, and only weakly in strains that contained the DmCdc2 bait, one of the two Drosophila Cdc2 homologs (Jimenez et al., EMBO J. 9:3565–3571, 1990; Lehner and O'Farrell, EMBO J. 9:3573–3581, 1990). In strains that contained the DMCdc2c bait or Fus3, Cdi1 did not activate at all. Since baits in this panel were related in sequence, were made from the same vector, were translated from a message that had the same 5' untranslated sequence and the same LexA coding sequence, and were expressed in yeast in the same amounts, the differences in transcription among the bait strains very likely reflected differences in interaction with the tagged Cdi1.

In order to identify residues on Cdc2 proteins that Cdi1 might recognize, the transcription interaction data was compared to the sequence of the baits. A lineup of the bait sequences was searched for residues that were conserved in the proteins with which Cdi1 interacted, but which differed in the proteins that Cdi1 did not touch. Use of this criterion identified 7 residues, which are indicated by asterisks in FIG. 10. Of these residues, two, Glu 57 and Gly 154 (in human Cdc2), are altered in the non-interacting baits to amino acids of different chemical type. In DmCdc2c, residue 57 is changed from Glu to Asn, and residue 154 from Gly to Asn; in Fus3, these residues are changed to His and Asp. In human Cdc2, both of these residues adjoin regions of the molecule necessary for interaction with cyclins (Ducommun et al., Mol. Cell. Biol. 11:6177–6184, 1991). Projection of the human Cdc2 primary sequence on the crystal structure solved by Knighton et al. for bovine cAMP dependent protein kinase (Science 253:407–413, 1991) suggests that residues 57 and 154 are in fact likely to be close to these cyclin contact points in the folded protein.

These results are thus consistent with the idea that Cdi1 may exert its effects by changing the affinity of Cdc2 proteins for particular cyclins, thus potentially altering their substrate specificity.

In summary, Cdi1 is a protein which complexes with Cdc2 family proteins. It is expressed around the time of the G1 to S transition, and the above results suggest that it may negatively regulate passage of cells through this part of the cycle, thus linking the regulatory networks connecting extracellular signals with core cell cycle controls. If Cdi1 is in fact a negative regulator, it is interesting to note that its normal function may be to convey signals that retard or block the cell cycle during G1. Since both normal differentiation and cancer can be considered consequences of changes in G1 regulation, this idea raises the possibilities that Cdi1 may function to remove cells from active cycle to allow differentiation (Pardee, Science 246:603–608, 1989); and that there are cancers in which lesions in the G1 regulatory machinery prevent Cdi1 from exerting its full effect.

Experimental procedures

Bacteria and yeast

Manipulation of bacterial strains and of DNAs was by standard methods (see, e.g., Ausubel et al., Current Protocols in Molecular Biology, New York, John Wiley & Sons, 1987; and Sambrook et al., Molecular Cloning: a Laboratory Manual, Cold Spring Harbor, N.Y., Cold Spring Harbor Laboratory, 1989) unless otherwise noted. E. coli "Sure" mcrA Δ(mrr, hsdRMS, mcrBC) endA1 supE44 thi-1 gyrA96 relA1 lac recB recJ sbcC umuC::Tn5($kan^R$) uvrC/F'[proAB, $lacI^qZ\Delta_{M15}$]::Tn10($tet^R$) (Stratagene Inc., LaJolla, Calif.) and KC8 (pyrF::Tn5 hsdR leuB600 trpC9830 lacΔ74 strA galK hisB436) were used as bacterial hosts throughout.

To determine whether Cdi1 complemented either G1 or G2 functions of cdc28, the following yeast strains were used: cdc28-1N (MATa ura3 ade1 trp1 cdc28-1N), which at the restrictive temperature arrests predominantly in G2; and cdc28-13 (MATα leu2 trp1 his3 ura3 ade1 tyr1 cdc28-13) and cdc28-17 (MATa leu2 trp1 his3 ura3 met14 arg5 arg6 tyr1 cdc28-17), which at the restrictive temperature arrests predominantly during G1.

Into these strains was introduced pJG4-6Cdi1 (see below), a yeast expression plasmid that directs the synthesis of Cdi1 that contains a hemagglutinin epitope tag at its amino terminus, and pJG4-7Cks2 (derived from the same selection) as a positive control. Overnight cultures of these strains were diluted 20:1 into trp⁻ complete minimal medium with 2% glucose and 2% galactose and grown at 25° C. for five hours. Dilutions of these cultures were plated onto duplicate plates of solid media that contained the same carbon sources; one plate was placed at 25° C. and the other at 36° C. Colonies were counted after five days of incubation In order to determine whether Cdi1 complemented a strain deficient in G1 cyclins, strain 3c-1AX (MATa bar1 Δcln1 Δcln2 Δcln3 cyh2 trp1 leu2 ura2 ade1 his2 [pLEU2-CYH2 ($CYH^s$)-$CLN3^+$]) into which pJG4-7Cdi1 or a GAL1-CLN3 construct as a positive control had been introduced was used. Overnight cultures were diluted into glucose and galactose medium as above, and grown for five hours at 30° C. Cells were plated onto glucose- and galactose-containing medium as above, except that the medium also contained 10 µg/ml cyclohexamide; cells were grown for three days and counted. Colonies can only arise on this medium when the CYH$^s$-CLN3$^+$ plasmid is lost, an event which itself can only occur if the other plasmid rescues the Cln deficiency.

The ability of Cdi1 to cause resistance to arrest by α factor was tested using a derivative of W303 (MATa trp1 ura3 his3 leu2 can1 bar1::LEU2) into which pJG4-4Cdi1, a plasmid that directs the synthesis of native Cdi1, had been introduced. Strain W303 was also transformed with a set of mammalian cDNAs that had been isolated by their ability to confer α factor resistance as a positive control. Overnight cultures were grown in glucose and galactose as above, and then plated on glucose and galactose medium, in the presence and absence of $10^{-7}$M α factor. Colonies were counted after 3 days.

For the growth rate experiments, W303 contained either pJG4-4Cdi1 or a vector control, in combination with either a pJG14-2, a HIS3$^+$ plasmid which directs the synthesis in yeast of native human Cdc2 under the control of the ADH1 promoter, or a vector control. Overnight cultures which were grown in His$^-$ Trp$^-$ minimal medium that contained 2% raffinose were collected, washed, and diluted into fresh medium that contained either 2% glucose or 1% galactose+ 1% raffinose to $OD_{600}$=0.1. Growth kinetics were followed, measuring the OD of aliquots taken every 2 hours.

Baits

In order to optimize operator occupancy, baits were produced constitutively under the control of the ADH1 promoter (Ammerer, Meth. Enzym. 101:192–210, 1983), and contained the LexA C-terminal oligomerization region, which contributes to operator occupancy by LexA-containing proteins, perhaps because it aids in the precise alignment of LexA amino termini of adjacent operator half sites (Golemis and Brent, Mol. Cell. Biol. 12:3006–3014, 1992). It is worth noting that all LexA-bait proteins so far examined enter the yeast nucleus in concentrations sufficient to permit operator binding, even though LexA derivatives are not specifically localized to the nucleus unless they contain other nuclear localization signals (see, e.g., Silver et al., Mol. Cell. Biol. 6:4763–4766, 1986).

pL202pl has been described (Ruden et al., Nature 350:426–430, 1991). This plasmid, a close relative of pMA424 and pSH2-1 (Ma and Ptashne, Cell 51:113–119, 1987; Hanes and Brent, Cell 57:1275–1283, 1989) carries the HIS3$^+$ marker and the 2µ replicator, and directs the synthesis in yeast of fusion proteins that carry the wild-type LexA protein at their amino terminus. Baits used in this study were made as follows: human Cdc2 (Lee and Nurse, Nature 327:31–35, 1987), Cdk2 (Tsai et al., Nature 353:174–177, 1991) and the *S. cerevisiae* CDC28 genes (Lorincz and Reed, Nature 307:183–185, 1984) were amplified by PCR using Vent polymerase (New England Biolabs, Beverley, Mass.) and cloned into pL202pl as EcoRI-BamHI fragments. These proteins contained two amino acids (glu phe) inserted between the last amino acid of LexA and the bait proteins. The Drosophila Cdc2 (Jimenez et al., EMBO J. 9:3565–3571, 1990; Lehner and O'Farrell, EMBO J. 9:3573–3581, 1990) baits were cloned as BamHI-SalI fragments following PCR amplification. LexA-Fus3 (Elion, Cell 60:649–664, 1990) and LexA-Cln3 (Cross, Mol. Cell. Biol 8:4675–4684, 1988, Nash et al., EMBO J. 7:4335–4346, 1988) were made in a similar way except they were cloned as BamHI fragments. These plasmids contained five amino acids (glu phe pro gly ile) (SEQ ID NO:2) inserted between LexA and the baits. All these fusions contained the entire coding region from the second amino acid to the stop codon. LexA-cMyc-Cterm contained the carboxy-terminal 176 amino acids of human cMyc, and LexA-Max contained all of the human Max coding sequence. LexA-Bicoid (amino acid 2-160) has been described (Golemis and Brent, Mol. Cell. Biol. 12:3006–3014, 1992).

Reporters

In the interaction trap, one reporter, the LexAop-LEU2 construction, replaced the yeast chromosomal LEU2 gene. The other reporter, one of a series of LexAop-GAL1-lacZ genes (Brent and Ptashne, Cell 43:729–736, 1985; Kamens et al., Mol. Cell. Biol. 10:2840–2847, 1990), was carried on a 2µ plasmid. The reporters were designed so that their basal transcription was extremely low, presumably due both to the removal of the entirety of the UAS from both reporters, and to the fact (whose cause is unknown) that LexA operators introduced into promoters tend to decrease transcription (Brent and Ptashne, Nature 312:612–615, 1984; Lech, Gene activation by DNA-bound Fos and Myc proteins. Ph.D. thesis, Harvard University, 1990). Reporters were selected to differ in their response to activation by LexA fusion proteins. In this study, the LEU2 reporter contained three copies of the high-affinity LexA binding site found upstream of *E. coli* colE1 (Ebina et al., J. Biol. Chem. 258:13258–13261, 1983; Kamens et al., Mol. Cell. Biol. 10:2840–2847, 1990), and thus presumably binds a total of 6 dimers of the bait. In contrast, the lacZ gene employed in the primary screen contained a single lower affinity consensus operator (Brent and Ptashne, Nature 312:612–615, 1984) which binds a single dimer of the bait. The LexA operators in the LEU2 reporter were closer to the transcription startpoint than they were in the lacZ reporter. These differences in the number, affinity, and position of the operators all contributed to making the LEU2 gene a more sensitive indicator than the lacZ gene, a property that is useful for this method.

p1840 and pJK103 have been described (Brent and Ptashne, Cell 43:729–736, 1985, Kamens et al., Mol. Cell. Biol. 10:2840–2847, 1990). pHR33 (Ellerstrom et al., Plant Mol. Biol. 18:557–566, 1992) was cut with HindIII and an ~1166 bp fragment that contained the URA3$^+$ gene from yEP24M13-2, a derivative of yEP24, was introduced into it to create pLEU2-0. This plasmid contains a BglII site 87 nucleotides upstream of the major LEU2 transcription startpoint. pLEU2-0 was cut with BglII, and a 42 bp double stranded BglII-ended oligomer

```
5' GATCCTGCTGTATATAAACCAGTGGTTATATGTACAGTACG 3' (SEQ ID NO 3)
3' GACGACATATATTTTGGTCACCAATATACATGTCATGCCTAG 5' (SEQ ID NO: 4)
``` that contains the overlapping LexA operators found upstream of the colecin E1 gene (Ebina et al., J. Biol. Chem. 258:13258–13261, 1983) and which presumably binds 2 LexA dimers, was introduced into it. One plasmid, pLEU2-LexAop6, that contained three copies of this oligomer was picked; it presumably binds 6 dimers of LexA fusion proteins.

Selection strains

EGY12 (MATa trp1 ura2 LEU2::pLEU2-0 (ΔUASLEU2)) and EGY38 (as above but::pLEU2-Lex-Aop6) were constructed as follows. pLEU2-0 and pLEU2-LexAop6 were linearized by digestion with ClaI within the LEU2 gene, and the DNA was introduced into U457 (MATa SUP53-a ade2-1 can1-100 ura3-52 trp1-1 [phi+]) by lithium acetate transformation (Ito et al., J. Bacter. 153:163–168, 1983); ura$^+$ colonies, which presumably contained the plasmid DNA integrated into LEU2, were selected. Several of these transformants were grown in YPD. Ura$^-$ cells were selected by plating these cultures on medium that contained 5-FOA (Ausubel et al., *Current Protocols in Molecular Biology*, New York, John Wiley & Sons, 1987). Both plasmids carry a TY1 element. For each integration, some of the ura3$^-$ revertants were also trp1$^-$, suggesting that the URA3$^+$ marker was deleted in a homologous recombination event that involved the TY1 sequences on the LEU2 plasmids and the chromosomal TY1 element upstream of SUP53-a (Oliver et al., Nature 357:38–46, 1992). Trp$^-$ colonies from each integration, EGY12 (no LexA operators) and EGY38 (6 operators) were saved. These were mated to GG100-14D (MATα his3 trp1 pho5). The resulting diploids were sporulated, and a number of random (MATα leu2– ura3– trp1– his3– GAL+) spore products were recovered. EGY40 and EGY48 are products of this cross; EGY40 has no LexA operators, EGY48 has 6. To make the bait strains, EGY48 was transformed with p1840 or pJK103 and with the different bait plasmids. Double transformants were selected on Glucose Ura$^-$ His$^-$ plates, and expression of the bait protein confirmed by Western blotting using anti-LexA antibody and standard techniques.

Library ("prey") expression vectors

Library-encoded proteins were expressed from pJG45, a member of a series of expression plasmids designed to be used in the interaction trap and to facilitate analysis of isolated proteins. These plasmids all carried the 2μ replicator, to ensure high copy number in yeast, and the TRP1 marker. pJG4-5 was designed to possess the following features: a galactose-inducible promoter to allow conditional expression of the library proteins, an epitope tag to facilitate their detection, a nuclear localization signal to maximize their intranuclear concentration in order to increase the sensitivity of the selection, and a weak acid blob activation domain (Ma and Ptashne, Cell 51:113–119, 1987). This domain was chosen for two reasons: because its activity is not subject to known regulation by yeast proteins as is the major GAL4 activation domain, and, more importantly, because it is a weak activator, presumably avoiding toxicity due to squelching or other mechanisms (Gill and Ptashne, Nature 334:721–724, 1988, Berger et al., Cell 70:251–265, 1992) very likely to restrict the number or type of interacting proteins recovered.

pJG4-5 was constructed as follows. An "expression cassette" containing the GAL1 promoter and the ADH1 terminator and a 345 nt insert that encoded a 107 amino acid moiety was inserted into pJG4-0, a plasmid that carries the TRP1 gene, the 2μ replicator, the pUC13 replication origin, and the ampicillin resistance gene. The pJG4-5 expression cassette directed the synthesis of fusion proteins, each of which carried at the amino terminus, amino to carboxy terminal, an ATG, an SV40 nuclear localization sequence (PPKKKRKVA) (SEQ ID NO: 5) (Kalderon et al., Cell 39:499–509, 1984), the B42 acid blob transcriptional activation domain (Ma and Ptashne, Cell 51:113–119, 1987) and the HA1 epitope tag (YPYDVPDYA) (SEQ ID NO: 6) (Green et al., Cell 28:477–487, 1980) (FIG. 3C). In addition to this plasmid, these experiments used two Cdi1 expression plasmids. EcoR1-XhoI Cdi1-containing fragments were introduced into pJG4-4 to make the plasmid pJG4-4Cdi1; Cdi1 was transcribed from this plasmid as a native, unfused protein under the control of the GAL1 promoter. EcoRI-XhoI Cdi1-containing fragments were also introduced into pJG4-6 to make the plasmid pJG4-6Cdi1; in this case, Cdi1 was expressed as an in-frame fusion containing, at its amino terminus, an ATG initiation codon and the hemagglutinin epitope tag.

Library construction

The activation-tagged yeast cDNA expression library was made from RNA isolated from serum grown, proliferating HeLa cells that were grown on plates to 70% confluence. Total RNA was extracted as described in Chomczynski and Sacchi (Anal. Biochem. 162:156–159, 1987), and polyA$^+$ mRNA was purified on an oligodT-cellulose column. cDNA synthesis was performed according to Gubler and Hoffman (Gene 25:263–269, 1983) as modified by Huse and Hansen (Strategies 1:1–3, 1988) using a linker primer that contained, 5' to 3' an 18 nt polydT tract, an XhoI site, and a 25 nt long GA rich sequence to protect the XhoI site. To protect any internal XhoI sites, the first strand was synthesized in the presence of 5'-methyl-CTP (instead of CTP) with an RNAse Hdefective version of the Moloney virus reverse transcriptase (Superscript, BRL, Grand Island, N.Y.). For second strand synthesis, the mRNA/cDNA hybrid was treated with RNAseH and *E. coli* DNA polymerase I, and the resulting ends were made flush by sequential treatment with Klenow, Mung Bean exonuclease, and Klenow onto which EcoRI adaptors:

5' AATTCGGCACGAGGCG 3' (SEQ ID NO: 7)
3' GCCGTGCTCCGC 5' (SEQ ID NO: 8)

were ligated, and the cDNA was digested with XhoI. This DNA was further purified on a Sephacryl S-400 spin column in order to remove excess adaptor sequences, and fractionated on a 5–20% KoAc gradient. Fractions containing >700 bp cDNAs were collected, and approximately ⅓ of the cDNA was ligated into EcoRI- and XhoI-digested pJG4-5. This ligation mixture was introduced into *E. coli* SURE cells by electroporation (Gene-Pulser, Bio-Rad, Hercules, Calif.) according to the manufacturer's instructions. 9.6×10$^6$ primary transformants were collected by scraping LB ampicillin plates. Colonies were pooled and grown in 6 liters of LB medium overnight (approximately three generations), and plasmid DNA was purified sequentially by standard techniques on two CsCl gradients. Digestion of transformants of individual library members with EcoR1 and XhoI revealed that >90% of the library members contained a cDNA insert whose typical size ranged between 1 kb–2 kb. Western blots of individual yeast transformants using the anti-hemagglutinin monoclonal antibody suggested that between ¼ and ⅓ of the members expressed fusion proteins.

Selection of Cdc2 interactors

Library transformation of the above-described strain was performed according to the procedure described by Ito et al. (J. Bacter. 153:163–168, 1983), except that the cells were grown to a higher OD as described in Schiestl and Gietz (Curr. Genet 16:339–346, 1989) and single stranded carrier DNA was included in the transformation mix also as described in Schiestl and Gietz (Curr. Genet 16:339–346, 1989). This procedure gave 1.2×10$^6$ primary library transformants (10$^4$ library transformants/μg DNA). Transformants were selected on Glucose Ura⁻ His⁻ Trp⁻ plates, scraped, suspended in approximately 20 ml of 65% glycerol, 10 mM Tris-HCl pH 7.5, 10 mM MgCl$_2$, and stored in 1 ml aliquots at −80°. Plating efficiency was determined on Galactose Ura⁻ His⁻ Trp⁻ after growing 50 μl of a cell suspension in 5 ml YP in the presence of 2% galactose. For screening the library, approximately 20 colony forming units on this medium/original transformant (about 2×10$^7$ cells) were plated on 4 standard circular 10 cm Galactose Ura⁻ His⁻ Trp⁻ Leu⁻ plates after the YP/galactose induction described above.

412 Leu⁺ colonies appeared after a 4 day incubation at 30° C. These colonies were collected on Glucose Ura⁻ His⁻ Trp⁻ master plates and retested on Glucose Ura⁻ His⁻ Trp⁻ Leu⁻, Galactose Ura⁻ His⁻ Trp⁻ Leu⁻, Glucose Xgal Ura⁻ His⁻ Trp⁻, and Galactose Xgal Ura⁻ His⁻ Trp⁻ plates. 55 of these colonies showed galactose-dependent growth on leu⁻ media and galactose-dependent blue color on Xgal medium, and were analyzed further.

Plasmid DNAs from these colonies were rescued as described (Hoffman and Winston, Gene 57:267–272, 1987), introduced into the bacterial strain KC8, and transformants were collected on Trp⁻ ampicillin plates. Plasmid DNAs were analyzed and categorized by the pattern of restriction fragments they gave on 1.8% agarose ½× TBE gels after triple digestion with EcoRI and XhoI, and either AluI or HaeIII. Characteristic plasmids from different restriction map classes of these cDNAs were retransformed into derivatives of EGY48 that expressed a panel of different LexA fusion proteins. Plasmids that carried cDNAs whose encoded proteins interacted with the LexA-Cdc2 bait but not with other LexA fusion proteins, including LexA-Bicoid, LexA-Fus3, LexA-Cln3, LexA-cMyc-Cterm, and LexA-Max were characterized further.

Microscopy 5 ml cultures of yeast cells were grown in the appropriate complete minimal medium up OD$_{600}$=0.8–1 and sonicated in a short burst to disrupt the clumps (Ausubel et al., *Current Protocols in Molecular Biology*, New York, John Wiley & Sons, 1987). The cells were collected by centrifugation, washed in 1 ml TE, resuspended in 1 ml 70% ethanol, and shaken for 1 hour at room temperature to fix them, then collected and resuspended in TE. The fixed cells were either examined directly at 1000× magnification with a Zeiss Axioscope microscope under Nomarski optics or by fluorescence after staining with 2.5 μg/ml DAPI as described in Silver et al. (Mol. Cell. Biol. 6:4763–4766, 1986).

FACS analysis

Yeast cells were grown and fixed as described above and prepared for FACS analysis of DNA content essentially as in Lew et al. (Cell 63:317–328, 1992). After fixation the cells were collected and washed three times in 0.8 mls 50 mM Tris/HCl pH 8.0, then 200 μl 2 mg/ml RNaseA was added and incubated at 37° C. with continuous shaking for 5 hours. The cells were pelleted, resuspended in 0.5 ml of 5 mg/ml pepsin (freshly dissolved in 55 mM HCl) and incubated in a 37° waterbath for 30 minutes. The cells were spun down, washed with 1 ml of 200 mM Tris/HCl pH 7.5, 211 mM NaCl, 78 mM MgCl$_2$ and resuspended in the same buffer. 55 μl of 500 μg/ml propidium iodide was then added, and cells were stained overnight at 4° C. Typically 10,000–20,000 events were read and analysed in a Becton Dickinson Fluorescence Activated Cell Sorter (Becton Dickinson, Lincoln Park, N.J.) with a CellFIT Cell-Cycle Analysis program Version 2.01.2.

For FACS analysis of DNA content, HeLa cells were grown on plates and transfected (Ausubel et al., *Current Protocols in Molecular Biology*, New York, John Wiley & Sons, 1987) either with pBNCdi1, a DNA copy of a retroviral cloning vector (Morgenstern and Land, Nucl. Acids. Res. 18:3587–3596, 1990) that directs expression of native Cdi1 under the control of the MoMuLV promoter, or with the vector alone. Clones of transfected cells were selected by growth in medium that contained 400 μg/ml of G418; Cdi1 expression did not diminish the number of G418 resistant cells recovered. Individual clones of each transfection (about 20) were rescued and grown on plates in DMEM+ 10% calf serum, collected using 0.05% trypsin, 0.02% EDTA and washed once with 1× PBS. Cells from four clones derived from the Cdi1 transfection and four from the control transfection were suspended in 225 μl of 30 μg/ml trypsin dissolved in 3.4 mM citrate, 0.1% NP40, 1.5 mM spermine and 0.5 mM Tris, and incubated on a rotator for 10 minutes at room temperature. 188 μl of 0.5 mg/ml of trypsin inhibitor and 0.1 mg/ml RNAse A was then added and the suspension was vortexed. After adding 188 μl of 0.4 mg/ml of propidium iodide and 1 mg/ml spermine, the samples were incubated for 30 minutes at 4° C. FACS analysis was carried out as described above.

Cdi1 Polypeptides and Antibodies

Polypeptide Expression

In general, polypeptides according to the invention may be produced by transformation of a suitable host cell with all or part of a Cdi1-encoding cDNA fragment (e.g., the cDNA described above) in a suitable expression vehicle.

Those skilled in the field of molecular biology will understand that any of a wide variety of expression systems may be used to provide the recombinant protein. The precise host cell used is not critical to the invention. The Cdi1 polypeptide may be produced in a prokaryotic host (e.g., *E. coli*) or in a eukaryotic host (e.g., *Saccharomyces cerevisiae* or mammalian cells, e.g., COS 1, NIH 3T3, or HeLa cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1989). The method of transformation or transfection and the choice of expression vehicle will depend on the host system selected. Transformation and transfection methods are described, e.g., in Ausubel et al. (*Current Protocols in Molecular Biology*, John Wiley & Sons, New York, 1989); expression vehicles may be chosen from those provided, e.g., in Cloning Vectors: A Laboratory Manual (P. H. Pouwels et al., 1985, Supp. 1987).

One preferred expression system is the mouse 3T3 fibroblast host cell transfected with a pMAMneo expression vector (Clontech, Palo Alto, Calif.). pMAMneo provides: an RSV-LTR enhancer linked to a dexamethasone-inducible MMTV-LTR promotor, an SV40 origin of replication which allows replication in mammalian systems, a selectable neomycin gene, and SV40 splicing and polyadenylation sites. DNA encoding a Cdi1 polypeptide would be inserted into the pMAMneo vector in an orientation designed to allow expression. The recombinant Cdi1 protein would be isolated as described below. Other preferable host cells which may be used in conjunction with the pMAMneo expression vehicle include COS cells and CHO cells (ATCC Accession Nos. CRL 1650 and CCL 61, respectively).

Alternatively, a Cdi1 polypeptide is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the Cdi1 polypeptide is cloned into an expression vector which includes the dihydrofolate reductase (DHFR) gene. Integration of the plasmid and, therefore, the Cdi1-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV(A) (described in Ausubel et al., supra). Any of the host cells described above or, preferably, a DHFR-deficient CHO cell line (e.g., CHO DHFR⁻cells, ATCC Accession No. CRL 9096) are among the host cells preferred for DHFR selection of a stably-transfected cell line or DHFR-mediated gene amplification.

Once the recombinant Cdi1 protein is expressed, it is isolated, e.g., using affinity chromatography. In one example, an anti-Cdi1 antibody (e.g., produced as described herein) may be attached to a column and used to isolate the Cdi1 polypeptide. Lysis and fractionation of Cdi1-harboring cells prior to affinity chromatography may be performed by standard methods (see, e.g., Ausubel et al., supra). Alternatively, a Cdi1 fusion protein, for example, a Cdi1-maltose binding protein, a Cdi1-β-galactosidase, or a Cdi1-trpE fusion protein, may be constructed and used for isolation of Cdi1 protein (see, e.g., Ausubel et al., supra; New England Biolabs, Beverly, Mass.).

Once isolated, the recombinant protein can, if desired, be further purified, e.g., by high performance liquid chromatography (see, e.g., Fisher, Laboratory *Techniques In Biochemistry And Molecular Biology*, eds., Work and Burdon, Elsevier, 1980).

Polypeptides of the invention, particularly short Cdi1 fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful Cdi1 fragments or analogs (described below).

Anti-Cdi1 Antibodies

Human Cdi1 (or immunogenic fragments or analogues) may be used to raise antibodies useful in the invention; such polypeptides may be produced by recombinant or peptide synthetic techniques (see, e.g., *Solid Phase Peptide Synthesis*, supra; Ausubel et al., supra). The peptides may be coupled to a carrier protein, such as KLH as described in Ausubel et al, supra. The KLH-peptide is mixed with Freund's adjuvant and injected into guinea pigs, rats, or preferably rabbits. Antibodies may be purified by peptide antigen affinity chromatography.

Monoclonal antibodies may be prepared using the Cdi1 polypeptides described above and standard hybridoma technology (see, e.g., Kohler et al., Nature 256:495, 1975; Kohler et al., *Eur. J. Immunol.* 6:511, 1976; Kohler et al., *Eur. J. Immunol.* 6:292, 1976; Hammerling et al., In *Monoclonal Antibodies* and *T Cell Hybridomas*, Elsevier, New York, 1981; Ausubel et al., supra).

Once produced, polyclonal or monoclonal antibodies are tested for specific Cdi1 recognition by Western blot or immunoprecipitation analysis (by the methods described in Ausubel et al., supra). Antibodies which specifically recognize a Cdi1 polypeptide are considered to be useful in the invention; such antibodies may be used, e.g., in an immunoassay to monitor the level of Cdi1 produced by a mammal.

Therapeutic and Diagnostic Uses for the Cdi1 Polypeptide

Therapy

The Cdi1 polypeptide of the invention has been shown to interact with a key regulator of human cell division and to inhibit the in vivo proliferation of yeast and human cells. Because of its role in the control of cell division, Cdi1 is an unusually good candidate for an anti-cancer therapeutic. Preferably, this therapeutic is delivered as a sense or anti-sense RNA product, for example, by expression from a retroviral vector delivered, for example, to the bone marrow. Treatment may be combined with more traditional cancer therapies such as surgery, radiation, or other forms of chemotherapy.

Alternatively, using the interaction trap system described herein, a large number of potential drugs may be easily screened, e.g., in yeast, for those which increase or decrease the interaction between Cdi1 and Cdc2. Drugs which increase Cdc2:Cdi1 interaction would increase reporter gene expression in the instant system, and conversely drugs which decrease Cdc2:Cdi1 interaction would decrease reporter gene expression. Such drugs are then tested in animal models for efficacy and, if successful, may be used as anticancer therapeutics according to their normal dosage and route of administration.

Detection of A Malignant Condition

Cdi1 polypeptides may also find diagnostic use in the detection or monitoring of cancerous conditions. In particular, because Cdi1 is involved in the control of cell division, a change in the level of Cdi1 production may indicate a malignant or pre-malignant condition. Levels of Cdi1 expression may be assayed by any standard technique. For example, its expression in a biological sample (e.g., a biopsy) may be monitored by standard Northern blot analysis or may be aided by PCR (see, e.g., Ausubel et al., Supra; *PCR Technology: Principles and Applications* for DNA *Amplification*, ed., H. A. Ehrlich, Stockton Press, New York; and Yap and McGee, *Nucl. Acids. Res.* 19:4294, 1991). These techniques are enabled by the provision of the Cdi1 sequence.

Alternatively, immunoassays may be used to detect Cdi1 protein in a biological sample. Cdi1-specific polyclonal, or preferably monoclonal, antibodies (produced as described above) may be used in any standard immunoassay format (e.g., ELISA, Western blot, or RIA assay) to measure Cdi1 polypeptide levels; again comparison would be to wild type Cdi1 levels, and a change in Cdi1 production would be indicative of a malignant or pre-malignant condition. Examples of immunoassays are described, e.g., in Ausubel et al., supra. Immunohistochemical techniques may also be utilized for Cdi1 detection. For example, a tissue sample may be obtained from a patient, and a section stained for the presence of Cdi1 using an anti-Cdi1 antibody and any standard detection system (e.g., one which includes a secondary antibody conjugated to horseradish peroxidase). General guidance regarding such techniques can be found in, e.g., Bancroft and Stevens (*Theory and Practice of Histological Techniques*, Churchill Livingstone, 1982) and Ausubel et al. (Supra).

In one particular example, a diagnostic method may be targeted toward a determination of whether the Cdi1 gene of a mammal includes the N-terminal PEST domain-encoding sequence. Because this sequence is very likely to stabilize the Cdi1 protein, its deletion may result in altered cellular levels of Cdi1 polypeptide and therefore be indicative of a malignant or premalignant condition. PEST deletions may be identified either by standard nucleic acid or polypeptide analyses.

The Cdi1 polypeptide is also useful for identifying that compartment of a mammalian cell where important cell division control functions occur. Antibodies specific for Cdi1 may be produced as described above. The normal subcellular location of the protein is then determined either in situ or using fractionated cells by any standard immunological or immunohistochemical procedure (see, e.g., Ausubel et al., supra; Bancroft and Stevens, *Theory and Practice of Histological Techniques*, Churchill Livingstone, 1982).

The methods of the instant invention may be used to reduce or diagnose the disorders described herein in any mammal, for example, humans, domestic pets, or livestock. Where a non-human mammal is treated, the Cdi1 polypeptide or the antibody employed is preferably specific for that species.

Other Embodiments

In other embodiments, the invention includes any protein which is substantially homologous to human Cdi1 (FIG. 6, SEQ ID NO: 1); such homologs include other substantially pure naturally occurring mammalian Cdi1 proteins as well as allelic variations; natural mutants; induced mutants; proteins encoded by DNA that hybridizes to the Cdi1 sequence of FIG. 6 under high stringency conditions or low stringency conditions (e.g., washing at 2× SSC at 40° C. with a probe length of at least 40 nucleotides); and polypeptides or proteins specifically bound by antisera directed to a Cdi1 polypeptide, especially by antisera to the active site or to the Cdc2 binding domain of Cdi1. The term also includes chimeric polypeptides that include a Cdi1 fragment.

The invention further includes analogs of any naturally occurring Cdi1 polypeptide. Analogs can differ from the naturally occurring Cdi1 protein by amino acid sequence differences, by post-translational modifications, or by both. Analogs of the invention will generally exhibit at least 70%, more preferably 80%, even more preferably 90%, and most preferably 95% or even 99%, homology with all or part of a naturally occurring Cdi1 sequence. The length of comparison sequences will be at least 8 amino acid residues, preferably at least 24 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally occurring Cdi1 polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, hereby incorporated by reference; or Ausubel et al., *Current Protocols in Molecular Biology*, John Wiley & Sons, 1989, hereby incorporated by reference). Also included are cyclized peptides molecules and analogs which contain residues other than L-amino acids, e.g., D-amino acids or non-naturally occurring or synthetic amino acids, e.g., β or γ amino acids.

In addition to full-length polypeptides, the invention also includes Cdi1 polypeptide fragments. As used herein, the term "fragment", means at least 10 contiguous amino acids, preferably at least 30 contiguous amino acids, more preferably at least 50 contiguous amino acids, and most preferably at least 60 to 80 or more contiguous amino acids. Fragments of Cdi1 can be generated by methods known to those skilled in the art or may result from normal protein processing (e.g., removal of amino acids from the nascent polypeptide that are not required for biological activity or removal of amino acids by alternative mRNA splicing or alternative protein processing events).

Preferable fragments or analogs according to the invention are those which exhibit biological activity (for example, the ability to interfere with mammalian cell division as assayed herein). Preferably, a Cdi1 polypeptide, fragment, or analog exhibits at least 10%, more preferably 30%, and most preferably, 70% or more of the biological activity of a full length naturally occurring Cdi1 polypeptide.

Other embodiments are within the following claims.

What is claimed is:

1. A method for determining whether a first protein is capable of physically interacting with a second protein, comprising:
   (a) providing a host cell which contains
      (i) a reporter gene operably linked to a DNA sequence comprising a protein binding site;
      (ii) a first fusion gene which expresses a first fusion protein, said first fusion protein comprising said first protein covalently bonded to a binding moiety which is capable of specifically binding to said protein binding site; and
      (iii) a second fusion gene which expresses a second fusion protein, said second fusion protein comprising said second protein covalently bonded to a weak gene activating moiety;
   (b) allowing said first protein and said second protein to interact; and
   (c) measuring expression of said reporter gene as a measure of said interaction between said first and said second proteins.

2. The method of claim 1, further comprising isolating the gene encoding said second protein.

3. The method of claim 1, wherein said weak gene activating moiety is the B42 activation domain.

4. The method of claim 1, wherein said host cell is a yeast cell.

5. The method of claim 1, wherein said reporter gene comprises the LEU2 gene.

6. The method of claim 1, wherein said reporter gene comprises the lacZ gene.

7. The method of claim 1, wherein said host cell further contains a second reporter gene operably linked to a DNA sequence comprising a protein binding site, both said binding sites being specifically bound by the same said first fusion protein binding moiety.

8. The method of claim 7, wherein the reporter genes comprise a LEU2 gene and a lacZ gene.

9. The method of claim 1, wherein said protein binding site is a LexA binding site and said binding moiety comprises a LexA DNA binding domain.

10. The method of claim 1, wherein said second protein is a protein involved in the control of eukaryotic cell division.

11. The method of claim 10, wherein said cell division control protein is encoded by a Cdc2 gene.

12. The method of claim 1, wherein said first fusion protein or said second fusion protein or both further comprise a nuclear localization sequence.

13. The method of claim 1, wherein said second fusion protein is conditionally expressed using an inducible promoter.

14. The method of claim 1, wherein said weak gene activating moiety is positioned at the amino terminus of said second fusion protein.

15. The method of claim 1, wherein said reporter gene exhibits no detectable basal gene expression.

16. The method of claim 7, wherein the phenotype of said reporter gene provides the basis for a selection and the phenotype of said second reporter gene provides the basis for a screen.

17. The method of claim 7, wherein said reporter gene and said second reporter gene differ from each other in levels of sensitivity.

18. The method of claim 1, wherein said first fusion protein or said second fusion protein or both further comprise an epitope tag to facilitate detection of fusion protein expression.

19. The method of claim 9, wherein said LexA DNA binding domain further comprises a LexA dimerization domain.

20. The method of claim 9, wherein said reporter gene is operably linked to multiple said LexA binding sites.

21. The method of claim 9, wherein said LexA binding sites are high affinity LexA binding sites.

22. A system for determining whether a first protein is capable of physically interacting with a second protein, comprising:
   (a) a host cell which contains
      (i) a reporter gene operably linked to a DNA sequence comprising a protein binding site;

(ii) a first fusion gene which expresses a first fusion protein, said first fusion protein comprising said first protein covalently bonded to a binding moiety which is capable of specifically binding to said protein binding site; and (iii) a second fusion gene which expresses a second fusion protein, said second fusion protein comprising said second protein covalently bonded to a weak gene activating moiety; and (b) means for measuring expression of said reporter gene, whereby said reporter gene expression is an indication of an interaction between said first and said second proteins.

23. The system of claim 22, wherein said weak gene activating moiety is the B42 activation domain.

24. The system of claim 22, wherein said host cell is a yeast cell.

25. The system of claim 22, wherein said reporter gene comprises the LEU2 gene.

26. The system of claim 22, wherein said reporter gene comprises the lacZ gene.

27. The system of claim 22, wherein said host cell further contains a second reporter gene operably linked to a DNA sequence comprising a protein binding site, both said protein binding sites being specifically bound by the same said first fusion protein binding moiety.

28. The system of claim 27, wherein the phenotype of said reporter gene provides the basis for a selection and the phenotype of said second reporter gene provides the basis for a screen.

29. The system of claim 27, wherein said reporter gene and said second reporter gene differ from each other in levels of sensitivity.

30. The system of claim 27, wherein the reporter genes comprise a LEU2 gene and a lacZ gene.

31. The system of claim 22, wherein said protein binding site is a LexA binding site and said binding moiety comprises a LexA DNA binding domain.

32. The system of claim 31, wherein said LexA DNA binding domain further comprises a LexA dimerization domain.

33. The system of claim 31, wherein said reporter gene is operably linked to multiple said LexA binding sites.

34. The system of claim 31, wherein said LexA binding sites are high affinity LexA binding sites.

35. The system of claim 22, wherein said first fusion protein or said second fusion protein or both further comprise a nuclear localization sequence.

36. The system of claim 22, wherein said second fusion protein is conditionally expressed using an inducible promoter.

37. The system of claim 22, wherein said weak gene activating moiety is positioned at the amino terminus of said second fusion protein.

38. The system of claim 22, wherein said reporter gene exhibits no detectable basal gene expression.

39. The system of claim 22, wherein said first fusion protein or said second fusion protein or both further comprise an epitope tag to facilitate detection of fusion protein expression.

40. The system of claim 22, wherein said second protein is a protein involved in the control of eukaryotic cell division.

41. The system of claim 40, wherein said cell division control protein is encoded by a Cdc2 gene.

\* \* \* \* \*

UNITED STATES PATENT AND TRADEMARK OFFICE
CERTIFICATE OF CORRECTION

PATENT NO. : 5,580,736
DATED : December 3, 1996
INVENTORS : Roger Brent, et al

It is certified that error appears in the above-identified patent and that said Letters Patent is hereby corrected as shown below:

Column 4, line 2, replace "measured Using" with --measured using--;

Column 10, line 67, replace "of these colonies" with --55 of these colonies--;

Column 11, line 46, replace "dimished" with --diminished--;

Column 20, line 26, replace "RNAse Hdefective" with --RNAseH defective--.

Signed and Sealed this

Fourth Day of November, 1997

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 33

( 2 ) INFORMATION FOR SEQ ID NO: 1:

( i ) SEQUENCE CHARACTERISTICS:
        ( A ) LENGTH: 804
        ( B ) TYPE: nucleic acid
        ( C ) STRANDEDNESS: double
        ( D ) TOPOLOGY: linear ( x i ) SEQUENCE DESCRIPTION: SEQ ID NO: 1:

```
GGC  ACT  GGT  CTC  GAC  GTG  GGG  CGG  CCA  GCG  ATG  GAG  CCG  CCC  AGT  TCA      48
Gly  Thr  Gly  Leu  Asp  Val  Gly  Arg  Pro  Ala  Met  Glu  Pro  Pro  Ser  Ser
1              5                        10                      15

ATA  CAA  ACA  AGT  GAG  TTT  GAC  TCA  TCA  GAT  GAA  GAG  CCT  ATT  GAA  GAT      96
Ile  Gln  Thr  Ser  Glu  Phe  Asp  Ser  Ser  Asp  Glu  Glu  Pro  Ile  Glu  Asp
               20                       25                      30

GAA  CAG  ACT  CCA  ATT  CAT  ATA  TCA  TGG  CTA  TCT  TTG  TCA  CGA  GTG  AAT     144
```

|   |   |   |   |   |   |   |   |   |   |   |   |   |   |   |   |   |
|---|---|---|---|---|---|---|---|---|---|---|---|---|---|---|---|---|
| Glu | Gln | Thr 35 | Pro | Ile | His | Ile | Ser | Trp 40 | Leu | Ser | Leu | Ser | Arg 45 | Val | Asn | |
| TGT Cys | TCT Ser 50 | CAG Gln | TTT Phe | CTC Leu | GGT Gly | TTA Leu 55 | TGT Cys | GCT Ala | CTT Leu | CCA Pro | GGT Gly 60 | TGT Cys | AAA Lys | TTT Phe | AAA Lys | 192 |
| GAT Asp 65 | GTT Val | AGA Arg | AGA Arg | AAT Asn | GTC Val 70 | CAA Gln | AAA Lys | GAT Asp | ACA Thr | GAA Glu 75 | GAA Glu | CTA Leu | AAG Lys | AGC Ser | TGT Cys 80 | 240 |
| GGT Gly | ATA Ile | CAA Gln | GAC Asp | ATA Ile 85 | TTT Phe | GTT Val | TTC Phe | TGC Cys | ACC Thr 90 | AGA Arg | GGG Gly | GAA Glu | CTG Leu | TCA Ser 95 | AAA Lys | 288 |
| TAT Tyr | AGA Arg | GTC Val | CCA Pro 100 | AAC Asn | CTT Leu | CTG Leu | GAT Asp | CTC Leu 105 | TAC Tyr | CAG Gln | CAA Gln | TGT Cys | GGA Gly 110 | ATT Ile | ATC Ile | 336 |
| ACC Thr | CAT His | CAT His 115 | CAT His | CCA Pro | ATC Ile | GCA Ala | GAT Asp 120 | GGA Gly | GGG Gly | ACT Thr | CCT Pro | GAC Asp 125 | ATA Ile | GCC Ala | AGC Ser | 384 |
| TGC Cys | TGT Cys 130 | GAA Glu | ATA Ile | ATG Met | GAA Glu | GAG Glu 135 | CTT Leu | ACA Thr | ACC Thr | TGC Cys | CTT Leu 140 | AAA Lys | AAT Asn | TAC Tyr | CGA Arg | 432 |
| AAA Lys 145 | ACC Thr | TTA Leu | ATA Ile | CAC His | TGC Cys 150 | TAT Tyr | GGA Gly | GGA Gly | CTT Leu | GGG Gly 155 | AGA Arg | TCT Ser | TGT Cys | CTT Leu | GTA Val 160 | 480 |
| GCT Ala | GCT Ala | TGT Cys | CTC Leu | CTA Leu 165 | CTA Leu | TAC Tyr | CTG Leu | TCT Ser | GAC Asp 170 | ACA Thr | ATA Ile | TCA Ser | CCA Pro | GAG Glu 175 | CAA Gln | 528 |
| GCC Ala | ATA Ile | GAC Asp | AGC Ser 180 | CTG Leu | CGA Arg | GAC Asp | CTA Leu | AGA Arg 185 | GGA Gly | TCC Ser | GGG Gly | GCA Ala | ATA Ile 190 | CAG Gln | ACC Thr | 576 |
| ATC Ile | AAG Lys | CAA Gln 195 | TAC Tyr | AAT Asn | TAT Tyr | CTT Leu | CAT His 200 | GAG Glu | TTT Phe | CGG Arg | GAC Asp | AAA Lys 205 | TTA Leu | GCT Ala | GCA Ala | 624 |
| CAT His | CTA Leu 210 | TCA Ser | TCA Ser | AGA Arg | GAT Asp | TCA Ser 215 | CAA Gln | TCA Ser | AGA Arg | TCT Ser | GTA Val 220 | TCA Ser | AGA Arg | | | 666 |

```
TAAAGGAATT CAAATAGCAT ATATATGACC ATGTCTGAAA TGTCAGTTCT CTAGCATAAT    726

TTGTATTGAA ATGAAACCAC CAGTGTTATC AACTTGAATG TAAATGTACA TGTGCAGATA    786

TTCCTAAAGT TTTATTGA                                                  804
```

( 2 ) INFORMATION FOR SEQ ID NO: 2:

( i ) SEQUENCE CHARACTERISTICS:
( A ) LENGTH: 5
( B ) TYPE: amino acid
( C ) STRANDEDNESS:
( D ) TOPOLOGY: linear ( x i ) SEQUENCE DESCRIPTION: SEQ ID NO: 2:

Glu  Phe  Pro  Gly  Ile
 1                    5

( 2 ) INFORMATION FOR SEQ ID NO: 3:

( i ) SEQUENCE CHARACTERISTICS:
( A ) LENGTH: 42
( B ) TYPE: nucleic acid
( C ) STRANDEDNESS: double
( D ) TOPOLOGY: linear ( x i ) SEQUENCE DESCRIPTION: SEQ ID NO: 3:

```
GATCCTGCTG TATATAAAAC CAGTGGTTAT ATGTACAGTA CG                        42
```

( 2 ) INFORMATION FOR SEQ ID NO: 4:

( i ) SEQUENCE CHARACTERISTICS:
        ( A ) LENGTH: 42
        ( B ) TYPE: nucleic acid
        ( C ) STRANDEDNESS: double
        ( D ) TOPOLOGY: linear ( x i ) SEQUENCE DESCRIPTION: SEQ ID NO: 4:

GACGACATAT ATTTTGGTCA CCAATATACA TGTCATGCCT AG        42

( 2 ) INFORMATION FOR SEQ ID NO: 5:

( i ) SEQUENCE CHARACTERISTICS:
        ( A ) LENGTH: 9
        ( B ) TYPE: amino acid
        ( C ) STRANDEDNESS:
        ( D ) TOPOLOGY: linear ( x i ) SEQUENCE DESCRIPTION: SEQ ID NO: 5:

Pro Pro Lys Lys Lys Arg Lys Val Ala
 1               5

( 2 ) INFORMATION FOR SEQ ID NO: 6:

( i ) SEQUENCE CHARACTERISTICS:
        ( A ) LENGTH: 9
        ( B ) TYPE: amino acid
        ( C ) STRANDEDNESS:
        ( D ) TOPOLOGY: linear ( x i ) SEQUENCE DESCRIPTION: SEQ ID NO: 6:

Tyr Pro Tyr Asp Val Pro Asp Tyr Ala
 1               5

( 2 ) INFORMATION FOR SEQ ID NO: 7:

( i ) SEQUENCE CHARACTERISTICS:
        ( A ) LENGTH: 16
        ( B ) TYPE: nucleic acid
        ( C ) STRANDEDNESS: double
        ( D ) TOPOLOGY: linear ( x i ) SEQUENCE DESCRIPTION: SEQ ID NO: 7:

AATTCGGCAC GAGGCG        16

( 2 ) INFORMATION FOR SEQ ID NO: 8:

( i ) SEQUENCE CHARACTERISTICS:
        ( A ) LENGTH: 12
        ( B ) TYPE: nucleic acid
        ( C ) STRANDEDNESS: double
        ( D ) TOPOLOGY: linear ( x i ) SEQUENCE DESCRIPTION: SEQ ID NO: 8:

GCCGTGCTCC GC        12

( 2 ) INFORMATION FOR SEQ ID NO: 9:

( i ) SEQUENCE CHARACTERISTICS:
        ( A ) LENGTH: 73
        ( B ) TYPE: amino acid
        ( C ) STRANDEDNESS:
        ( D ) TOPOLOGY: linear ( x i ) SEQUENCE DESCRIPTION: SEQ ID NO: 9:

Met Glu Asp Tyr Thr Lys Ile Glu Lys Ile Gly Glu Gly Thr Tyr Gly
 1              5                  10                 15

```
Val  Val  Tyr  Lys  Gly  Arg  Lys  Lys  Thr  Thr  Gly  Gln  Val  Val  Ala  Met
               20                  25                       30

Lys  Lys  Ile  Arg  Leu  Glu  Ser  Glu  Glu  Gly  Val  Pro  Ser  Thr  Ala
               35                  40                       45

Ile  Arg  Glu  Ile  Ser  Leu  Leu  Lys  Glu  Leu  Arg  His  Pro  Asn  Ile  Val
          50                       55                       60

Ser  Leu  Gln  Asp  Val  Leu  Met  Gln  Asp
65                            70
```

( 2 ) INFORMATION FOR SEQ ID NO: 10:

( i ) SEQUENCE CHARACTERISTICS:
        ( A ) LENGTH: 73
        ( B ) TYPE: amino acid
        ( C ) STRANDEDNESS:
        ( D ) TOPOLOGY: linear ( x i ) SEQUENCE DESCRIPTION: SEQ ID NO: 10:

```
Met  Glu  Asn  Phe  Gln  Lys  Val  Glu  Lys  Ile  Gly  Glu  Gly  Thr  Tyr  Gly
1                        5                        10                       15

Val  Val  Tyr  Lys  Ala  Arg  Asn  Lys  Leu  Thr  Gly  Glu  Val  Val  Ala  Leu
               20                  25                       30

Lys  Lys  Ile  Arg  Leu  Asp  Thr  Glu  Thr  Glu  Gly  Val  Pro  Ser  Thr  Ala
               35                  40                       45

Ile  Arg  Glu  Ile  Ser  Leu  Leu  Lys  Glu  Leu  Asn  His  Pro  Asn  Ile  Val
          50                       55                       60

Lys  Leu  Leu  Asp  Val  Ile  His  Thr  Glu
65                            70
```

( 2 ) INFORMATION FOR SEQ ID NO: 11:

( i ) SEQUENCE CHARACTERISTICS:
        ( A ) LENGTH: 82
        ( B ) TYPE: amino acid
        ( C ) STRANDEDNESS:
        ( D ) TOPOLOGY: linear ( x i ) SEQUENCE DESCRIPTION: SEQ ID NO: 11:

```
Met  Ser  Gly  Glu  Leu  Ala  Asn  Tyr  Lys  Arg  Leu  Glu  Lys  Val  Gly  Glu
1                        5                        10                       15

Gly  Thr  Tyr  Gly  Val  Val  Tyr  Lys  Ala  Leu  Asp  Leu  Arg  Pro  Gly  Gln
               20                  25                       30

Gly  Gln  Arg  Val  Val  Ala  Leu  Leu  Lys  Lys  Ile  Arg  Leu  Glu  Ser  Glu
               35                  40                       45

Asp  Glu  Gly  Val  Pro  Ser  Thr  Ala  Ile  Arg  Glu  Ile  Ser  Leu  Leu  Lys
          50                       55                       60

Glu  Leu  Lys  Asp  Asp  Asn  Ile  Val  Arg  Leu  Tyr  Asp  Ile  Val  His  Ser
65                            70                       75                  80

Asp  Ala
```

( 2 ) INFORMATION FOR SEQ ID NO: 12:

( i ) SEQUENCE CHARACTERISTICS:
        ( A ) LENGTH: 73
        ( B ) TYPE: amino acid
        ( C ) STRANDEDNESS:
        ( D ) TOPOLOGY: linear ( x i ) SEQUENCE DESCRIPTION: SEQ ID NO: 12:

```
Met  Glu  Asp  Phe  Glu  Lys  Ile  Glu  Lys  Ile  Gly  Glu  Gly  Thr  Tyr  Gly
1                        5                        10                       15
```

```
Val  Val  Tyr  Lys  Gly  Arg  Asn  Arg  Leu  Thr  Gly  Gln  Ile  Val  Ala  Met
               20                       25                      30

Lys  Lys  Ile  Arg  Leu  Glu  Ser  Asp  Asp  Glu  Gly  Val  Pro  Ser  Thr  Ala
               35                       40                      45

Ile  Arg  Glu  Ile  Ser  Leu  Leu  Lys  Glu  Leu  Lys  His  Glu  Asn  Ile  Val
     50                       55                      60

Cys  Leu  Glu  Asp  Val  Leu  Met  Glu  Glu
65                       70
```

( 2 ) INFORMATION FOR SEQ ID NO: 13:

( i ) SEQUENCE CHARACTERISTICS:
        ( A ) LENGTH: 77
        ( B ) TYPE: amino acid
        ( C ) STRANDEDNESS:
        ( D ) TOPOLOGY: linear ( x i ) SEQUENCE DESCRIPTION: SEQ ID NO: 13:

```
Met  Thr  Thr  Ile  Leu  Asp  Asn  Phe  Gln  Arg  Ala  Glu  Lys  Ile  Gly  Glu
1                        5                       10                      15

Gly  Thr  Tyr  Gly  Ile  Val  Tyr  Lys  Ala  Arg  Ser  Asn  Ser  Thr  Gly  Gln
               20                       25                      30

Asp  Val  Ala  Leu  Lys  Lys  Ile  Arg  Glu  Leu  Gly  Glu  Thr  Glu  Gly  Val
               35                       40                      45

Pro  Ser  Thr  Ala  Ile  Arg  Glu  Ile  Ser  Leu  Leu  Lys  Asn  Leu  Lys  His
     50                       55                      60

Pro  Asn  Val  Val  Gln  Leu  Phe  Asp  Val  Val  Ile  Ser  Gly
65                       70                      75
```

( 2 ) INFORMATION FOR SEQ ID NO: 14:

( i ) SEQUENCE CHARACTERISTICS:
        ( A ) LENGTH: 86
        ( B ) TYPE: amino acid
        ( C ) STRANDEDNESS:
        ( D ) TOPOLOGY: linear ( x i ) SEQUENCE DESCRIPTION: SEQ ID NO: 14:

```
Met  Pro  Lys  Arg  Ile  Val  Tyr  Asn  Ile  Ser  Ser  Asp  Phe  Gln  Leu  Lys
1                        5                       10                      15

Ser  Leu  Leu  Gly  Glu  Gly  Ala  Tyr  Gly  Val  Val  Cys  Ser  Ala  Thr  His
               20                       25                      30

Lys  Pro  Thr  Gly  Glu  Ile  Val  Ala  Ile  Lys  Lys  Ile  Glu  Pro  Phe  Asp
               35                       40                      45

Lys  Pro  Leu  Phe  Ala  Leu  Arg  Thr  Leu  Arg  Glu  Ile  Lys  Ile  Leu  Lys
     50                       55                      60

His  Phe  Lys  His  Glu  Asn  Ile  Ile  Thr  Ile  Phe  Asn  Ile  Gln  Arg  Pro
65                       70                      75                      80

Asp  Ser  Phe  Glu  Asn  Phe
                    85
```

( 2 ) INFORMATION FOR SEQ ID NO: 15:

( i ) SEQUENCE CHARACTERISTICS:
        ( A ) LENGTH: 84
        ( B ) TYPE: amino acid
        ( C ) STRANDEDNESS:
        ( D ) TOPOLOGY: linear ( x i ) SEQUENCE DESCRIPTION: SEQ ID NO: 15:

```
Ser  Arg  Leu  Tyr  Leu  Ile  Phe  Glu  Phe  Leu  Ser  Met  Asp  Leu  Lys  Lys
```

```
            1               5                  10                    15

Tyr  Leu  Asp  Ser  Ile  Pro  Pro  Gly  Gln  Tyr  Met  Asp  Ser  Ser  Leu  Val
                    20                   25                    30

Lys  Ser  Tyr  Leu  Tyr  Gln  Ile  Leu  Gln  Gly  Ile  Val  Phe  Cys  His  Ser
               35                   40                    45

Arg  Arg  Val  Leu  His  Arg  Asp  Leu  Lys  Pro  Gln  Asn  Leu  Leu  Ile  Asp
          50                    55                    60

Asp  Lys  Gly  Thr  Ile  Lys  Leu  Ala  Asp  Phe  Gly  Leu  Ala  Arg  Ala  Phe
65                       70                    75                          80

Gly  Ile  Pro  Ile
```

(2) INFORMATION FOR SEQ ID NO: 16:

(i) SEQUENCE CHARACTERISTICS:
        (A) LENGTH: 83
        (B) TYPE: amino acid
        (C) STRANDEDNESS:
        (D) TOPOLOGY: linear (xi) SEQUENCE DESCRIPTION: SEQ ID NO: 16:

```
Asn  Lys  Leu  Tyr  Leu  Val  Phe  Glu  Phe  Leu  His  Gln  Asp  Leu  Lys  Lys
 1                   5                   10                     15

Phe  Met  Asp  Ala  Ser  Ala  Leu  Thr  Gly  Ile  Pro  Leu  Pro  Leu  Ile  Lys
                    20                   25                    30

Ser  Tyr  Leu  Phe  Gln  Leu  Leu  Gln  Gly  Leu  Ala  Pro  Cys  His  Ser  His
               35                   40                    45

Arg  Val  Leu  His  Arg  Asp  Leu  Lys  Pro  Gln  Asn  Leu  Leu  Ile  Asn  Thr
          50                    55                    60

Glu  Gly  Ala  Ile  Lys  Leu  Ala  Asp  Phe  Gly  Leu  Ala  Arg  Ala  Phe  Gly
65                       70                    75                          80

Val  Pro  Val
```

(2) INFORMATION FOR SEQ ID NO: 17:

(i) SEQUENCE CHARACTERISTICS:
        (A) LENGTH: 84
        (B) TYPE: amino acid
        (C) STRANDEDNESS:
        (D) TOPOLOGY: linear (xi) SEQUENCE DESCRIPTION: SEQ ID NO: 17:

```
His  Lys  Leu  Tyr  Leu  Val  Phe  Glu  Phe  Leu  Asp  Leu  Asp  Leu  Lys  Arg
 1                   5                   10                     15

Tyr  Met  Glu  Gly  Ile  Pro  Lys  Asp  Gln  Pro  Leu  Gly  Ala  Asp  Ile  Val
                    20                   25                    30

Lys  Lys  Phe  Met  Met  Gln  Leu  Cys  Lys  Gly  Ile  Ala  Tyr  Cys  His  Ser
               35                   40                    45

His  Arg  Ile  Leu  His  Arg  Asp  Leu  Lys  Pro  Gln  Asn  Leu  Leu  Ile  Asn
          50                    55                    60

Lys  Asp  Gly  Asn  Leu  Lys  Leu  Gly  Asp  Phe  Gly  Leu  Ala  Arg  Ala  Phe
65                       70                    75                          80

Gly  Val  Pro  Leu
```

(2) INFORMATION FOR SEQ ID NO: 18:

(i) SEQUENCE CHARACTERISTICS:
        (A) LENGTH: 84
        (B) TYPE: amino acid
        (C) STRANDEDNESS:
        (D) TOPOLOGY: linear ( x i ) SEQUENCE DESCRIPTION: SEQ ID NO: 18:

Asn Arg Ile Tyr Leu Ile Phe Glu Phe Leu Ser Met Asp Leu Lys Lys
1               5                   10                  15

Tyr Met Asp Ser Leu Pro Val Asp Lys His Met Glu Ser Glu Leu Val
            20                  25                  30

Arg Ser Tyr Leu Tyr Gln Ile Thr Ser Ala Ile Leu Phe Cys His Arg
        35                  40                  45

Arg Arg Val Leu His Arg Asp Leu Lys Pro Gln Asn Leu Leu Ile Asp
    50                  55                  60

Lys Ser Gly Leu Ile Lys Val Ala Asp Phe Gly Leu Gly Arg Ser Phe
65                  70                  75                  80

Gly Ile Pro Val ( 2 ) INFORMATION FOR SEQ ID NO: 19:

( i ) SEQUENCE CHARACTERISTICS:
        ( A ) LENGTH: 82
        ( B ) TYPE: amino acid
        ( C ) STRANDEDNESS:
        ( D ) TOPOLOGY: linear ( x i ) SEQUENCE DESCRIPTION: SEQ ID NO: 19:

Asn Asn Leu Tyr Met Ile Phe Glu Tyr Leu Asn Met Asp Leu Lys Lys
1               5                   10                  15

Leu Met Asp Lys Lys Lys Asp Val Phe Thr Pro Gln Leu Ile Lys Ser
            20                  25                  30

Tyr Met His Gln Ile Leu Asp Ala Val Gly Phe Cys His Thr Asn Arg
        35                  40                  45

Ile Leu His Arg Asp Leu Lys Pro Gln Asn Leu Leu Val Asp Thr Ala
    50                  55                  60

Gly Lys Ile Lys Leu Ala Asp Phe Gly Leu Ala Arg Ile Phe Asn Val
65                  70                  75                  80

Pro Met ( 2 ) INFORMATION FOR SEQ ID NO: 20:

( i ) SEQUENCE CHARACTERISTICS:
        ( A ) LENGTH: 86
        ( B ) TYPE: amino acid
        ( C ) STRANDEDNESS:
        ( D ) TOPOLOGY: linear ( x i ) SEQUENCE DESCRIPTION: SEQ ID NO: 20:

Asn Glu Val Tyr Ile Ile Gln Glu Leu Met Gln Thr Asp Leu His Arg
1               5                   10                  15

Val Ile Ser Thr Gln Met Leu Ser Asp Asp His Ile Gln Tyr Phe Ile
            20                  25                  30

Tyr Gln Thr Leu Arg Ala Val Lys Val Leu Glu Gly Ser Asn Val Ile
        35                  40                  45

His Arg Asp Leu Lys Pro Ser Asn Leu Leu Ile Asn Ser Asn Cys Asp
    50                  55                  60

Leu Lys Val Cys Asp Phe Gly Leu Ala Arg Ile Ile Asp Glu Ser Ala
65                  70                  75                  80

Ala Asp Asn Ser Glu Pro
                85

( 2 ) INFORMATION FOR SEQ ID NO: 21:

(i) SEQUENCE CHARACTERISTICS:
  (A) LENGTH: 83
  (B) TYPE: amino acid
  (C) STRANDEDNESS:
  (D) TOPOLOGY: linear (xi) SEQUENCE DESCRIPTION: SEQ ID NO: 21:

| Arg | Val | Tyr | Thr | His | Glu | Val | Val | Thr | Leu | Trp | Tyr | Arg | Ser | Pro | Glu |
|---|---|---|---|---|---|---|---|---|---|---|---|---|---|---|---|
| 1 | | | | 5 | | | | | 10 | | | | | 15 | |
| Val | Leu | Leu | Gly | Ser | Ala | Arg | Tyr | Ser | Thr | Pro | Val | Asp | Ile | Trp | Ser |
| | | | 20 | | | | | 25 | | | | | 30 | | |
| Ile | Gly | Thr | Ile | Phe | Ala | Glu | Leu | Ala | Thr | Lys | Lys | Pro | Leu | Phe | His |
| | | 35 | | | | | 40 | | | | | 45 | | | |
| Gly | Asp | Ser | Glu | Ile | Asp | Gln | Leu | Phe | Arg | Ile | Phe | Arg | Ala | Leu | Gly |
| | | 50 | | | | | 55 | | | | | 60 | | | |
| Thr | Pro | Asn | Asn | Glu | Val | Trp | Pro | Glu | Val | Glu | Ser | Leu | Gln | Asp | Tyr |
| 65 | | | | | 70 | | | | | 75 | | | | | 80 |
| Lys | Asn | Thr | | | | | | | | | | | | | |

(2) INFORMATION FOR SEQ ID NO: 22:

(i) SEQUENCE CHARACTERISTICS:
  (A) LENGTH: 83
  (B) TYPE: amino acid
  (C) STRANDEDNESS:
  (D) TOPOLOGY: linear (xi) SEQUENCE DESCRIPTION: SEQ ID NO: 22:

| Arg | Thr | Tyr | Thr | His | Glu | Val | Val | Thr | Leu | Trp | Tyr | Arg | Ala | Pro | Glu |
|---|---|---|---|---|---|---|---|---|---|---|---|---|---|---|---|
| 1 | | | | 5 | | | | | 10 | | | | | 15 | |
| Ile | Leu | Leu | Gly | Cys | Lys | Tyr | Tyr | Ser | Thr | Ala | Val | Asp | Ile | Trp | Ser |
| | | | 20 | | | | | 25 | | | | | 30 | | |
| Leu | Gly | Cys | Ile | Phe | Ala | Glu | Met | Val | Thr | Arg | Arg | Ala | Leu | Phe | Pro |
| | | 35 | | | | | 40 | | | | | 45 | | | |
| Gly | Asp | Ser | Glu | Ile | Asp | Gln | Leu | Phe | Arg | Ile | Phe | Arg | Thr | Leu | Gly |
| | | 50 | | | | | 55 | | | | | 60 | | | |
| Thr | Pro | Asp | Glu | Val | Val | Trp | Pro | Gly | Val | Thr | Ser | Met | Pro | Asp | Tyr |
| 65 | | | | | 70 | | | | | 75 | | | | | 80 |
| Lys | Pro | Ser | | | | | | | | | | | | | |

(2) INFORMATION FOR SEQ ID NO: 23:

(i) SEQUENCE CHARACTERISTICS:
  (A) LENGTH: 83
  (B) TYPE: amino acid
  (C) STRANDEDNESS:
  (D) TOPOLOGY: linear (xi) SEQUENCE DESCRIPTION: SEQ ID NO: 23:

| Arg | Ala | Tyr | Thr | His | Glu | Ile | Val | Thr | Leu | Trp | Tyr | Arg | Ala | Pro | Glu |
|---|---|---|---|---|---|---|---|---|---|---|---|---|---|---|---|
| 1 | | | | 5 | | | | | 10 | | | | | 15 | |
| Val | Leu | Leu | Gly | Gly | Lys | Gln | Tyr | Ser | Thr | Gly | Val | Asp | Thr | Trp | Ser |
| | | | 20 | | | | | 25 | | | | | 30 | | |
| Ile | Gly | Cys | Ile | Phe | Ala | Glu | Met | Cys | Asn | Arg | Lys | Pro | Ile | Phe | Ser |
| | | 35 | | | | | 40 | | | | | 45 | | | |
| Gly | Asp | Ser | Glu | Ile | Asp | Gln | Leu | Phe | Lys | Ile | Phe | Arg | Val | Leu | Gly |
| | | 50 | | | | | 55 | | | | | 60 | | | |
| Thr | Pro | Asn | Glu | Ala | Ile | Trp | Pro | Asp | Ile | Val | Tyr | Leu | Pro | Asp | Phe |
| 65 | | | | | 70 | | | | | 75 | | | | | 80 |
| Lys | Pro | Ser | | | | | | | | | | | | | |

( 2 ) INFORMATION FOR SEQ ID NO: 24:

( i ) SEQUENCE CHARACTERISTICS:
        ( A ) LENGTH: 83
        ( B ) TYPE: amino acid
        ( C ) STRANDEDNESS:
        ( D ) TOPOLOGY: linear ( x i ) SEQUENCE DESCRIPTION: SEQ ID NO: 24:

```
Arg Ile Tyr Thr His Glu Ile Val Thr Leu Trp Tyr Arg Ala Pro Glu
 1               5                  10                  15
Val Leu Leu Gly Ser Pro Arg Tyr Ser Cys Pro Val Asp Ile Trp Ser
            20                  25                  30
Ile Gly Cys Ile Phe Ala Glu Met Ala Thr Arg Lys Pro Leu Phe Gln
        35                  40                  45
Gly Asp Ser Glu Ile Asp Gln Leu Phe Lys Ile Phe Arg Val Leu Gly
    50                  55                  60
Thr Pro Asn Glu Ala Ile Trp Pro Asp Ile Val Tyr Leu Pro Asp Phe
65                  70                  75                  80
Lys Pro Ser
```

( 2 ) INFORMATION FOR SEQ ID NO: 25:

( i ) SEQUENCE CHARACTERISTICS:
        ( A ) LENGTH: 83
        ( B ) TYPE: amino acid
        ( C ) STRANDEDNESS:
        ( D ) TOPOLOGY: linear ( x i ) SEQUENCE DESCRIPTION: SEQ ID NO: 25:

```
Arg Ala Tyr Thr His Glu Val Val Thr Leu Trp Tyr Arg Ala Pro Glu
 1               5                  10                  15
Ile Leu Leu Gly Thr Lys Phe Tyr Ser Thr Gly Val Asp Ile Trp Ser
            20                  25                  30
Leu Gly Cys Ile Phe Ser Glu Met Ile Met Arg Arg Ser Leu Phe Pro
        35                  40                  45
Gly Asp Ser Glu Ile Asp Gln Leu Tyr Arg Ile Phe Arg Thr Leu Ser
    50                  55                  60
Thr Pro Asp Glu Thr Asn Trp Pro Gly Val Thr Gln Leu Pro Asp Phe
65                  70                  75                  80
Lys Thr Lys
```

( 2 ) INFORMATION FOR SEQ ID NO: 26:

( i ) SEQUENCE CHARACTERISTICS:
        ( A ) LENGTH: 90
        ( B ) TYPE: amino acid
        ( C ) STRANDEDNESS:
        ( D ) TOPOLOGY: linear ( x i ) SEQUENCE DESCRIPTION: SEQ ID NO: 26:

```
Thr Gly Gln Gln Ser Gly Met Thr Glu Tyr Val Ala Thr Arg Trp Tyr
 1               5                  10                  15
Arg Ala Pro Glu Val Met Leu Thr Ser Ala Lys Tyr Ser Arg Ala Met
            20                  25                  30
Asp Val Trp Ser Cys Gly Cys Ile Leu Ala Glu Leu Phe Leu Arg Arg
        35                  40                  45
Pro Ile Phe Pro Gly Arg Asp Tyr Arg His Gln Leu Leu Leu Ile Phe
    50                  55                  60
```

Gly Ile Ile Gly Thr Pro His Ser Asp Asn Asp Leu Arg Cys Ile Glu
65                  70                  75                  80

Ser Pro Arg Ala Arg Glu Tyr Ile Lys Ser
                85                  90

( 2 ) INFORMATION FOR SEQ ID NO: 27:

( i ) SEQUENCE CHARACTERISTICS:
    ( A ) LENGTH: 57
    ( B ) TYPE: amino acid
    ( C ) STRANDEDNESS:
    ( D ) TOPOLOGY: linear ( x i ) SEQUENCE DESCRIPTION: SEQ ID NO: 27:

Phe Pro Lys Trp Lys Pro Gly Ser Leu Ala Ser His Val Lys Asn Leu
1               5                   10                  15

Asp Glu Asn Gly Leu Asp Leu Leu Ser Lys Met Leu Ile Tyr Asp Pro
                20                  25                  30

Ala Lys Arg Ile Ser Gly Lys Met Ala Leu Asn His Pro Tyr Phe Asn
            35                  40                  45

Asp Leu Asp Asn Gln Ile Lys Lys Met
        50                  55

( 2 ) INFORMATION FOR SEQ ID NO: 28:

( i ) SEQUENCE CHARACTERISTICS:
    ( A ) LENGTH: 59
    ( B ) TYPE: amino acid
    ( C ) STRANDEDNESS:
    ( D ) TOPOLOGY: linear ( x i ) SEQUENCE DESCRIPTION: SEQ ID NO: 28:

Phe Pro Lys Trp Ala Arg Gln Asp Phe Ser Lys Val Val Pro Pro Leu
1               5                   10                  15

Asp Glu Asp Gly Ile Asp Leu Leu Asp Lys Leu Leu Ala Tyr Asp Pro
                20                  25                  30

Asn Lys Arg Ile Ser Ala Lys Ala Leu Ala His Pro Phe Thr Gln
            35                  40                  45

Asp Val Thr Lys Pro Val Pro His Leu Arg Leu
        50                  55

( 2 ) INFORMATION FOR SEQ ID NO: 29:

( i ) SEQUENCE CHARACTERISTICS:
    ( A ) LENGTH: 57
    ( B ) TYPE: amino acid
    ( C ) STRANDEDNESS:
    ( D ) TOPOLOGY: linear ( x i ) SEQUENCE DESCRIPTION: SEQ ID NO: 29:

Phe Pro Gln Trp Arg Arg Lys Asp Leu Ser Asn Gln Leu Lys Asn Leu
1               5                   10                  15

Asp Ala Asn Gly Ile Asp Leu Ile Gln Lys Met Leu Ile Tyr Asp Pro
                20                  25                  30

Val His Arg Ile Ser Ala Lys Asp Ile Leu Glu His Pro Tyr Phe Asn
            35                  40                  45

Gly Phe Gln Ser Gly Leu Val Arg Asn
        50                  55

( 2 ) INFORMATION FOR SEQ ID NO: 30:

( i ) SEQUENCE CHARACTERISTICS:
    ( A ) LENGTH: 57

(B) TYPE: amino acid
(C) STRANDEDNESS:
(D) TOPOLOGY: linear (xi) SEQUENCE DESCRIPTION: SEQ ID NO: 30:

| Phe | Pro | Gln | Trp | Arg | Arg | Lys | Asp | Leu | Ser | Asn | Gln | Leu | Lys | Asn | Leu |
| 1 | | | | 5 | | | | | 10 | | | | | 15 | |

| Asp | Ala | Asn | Gly | Ile | Asp | Leu | Ile | Gln | Lys | Met | Leu | Ile | Tyr | Asp | Pro |
| | | | 20 | | | | | 25 | | | | | 30 | | |

| Val | His | Arg | Ile | Ser | Ala | Lys | Asp | Ile | Leu | Glu | His | Pro | Tyr | Phe | Asn |
| | | 35 | | | | | 40 | | | | | 45 | | | |

| Gly | Phe | Gln | Ser | Gly | Leu | Val | Arg | Asn |
| | 50 | | | | | 55 | | |

(2) INFORMATION FOR SEQ ID NO: 31:

(i) SEQUENCE CHARACTERISTICS:
(A) LENGTH: 72
(B) TYPE: amino acid
(C) STRANDEDNESS:
(D) TOPOLOGY: linear (xi) SEQUENCE DESCRIPTION: SEQ ID NO: 31:

| Phe | Pro | Arg | Trp | Glu | Gly | Thr | Asn | Met | Pro | Gln | Pro | Ile | Thr | Glu | His |
| 1 | | | | 5 | | | | | 10 | | | | | 15 | |

| Glu | Ala | His | Glu | Leu | Ile | Met | Ser | Met | Leu | Cys | Tyr | Asp | Pro | Asn | Leu |
| | | | 20 | | | | | 25 | | | | | 30 | | |

| Arg | Ile | Ser | Ala | Lys | Asp | Ala | Leu | Gln | His | Ala | Tyr | Phe | Arg | Asn | Val |
| | | 35 | | | | | 40 | | | | | 45 | | | |

| Gln | His | Val | Asp | His | Val | Ala | Leu | Pro | Val | Asp | Pro | Asn | Ala | Gly | Ser |
| | 50 | | | | | 55 | | | | | 60 | | | | |

| Ala | Ser | Arg | Leu | Thr | Arg | Leu | Val |
| 65 | | | | | 70 | | |

(2) INFORMATION FOR SEQ ID NO: 32:

(i) SEQUENCE CHARACTERISTICS:
(A) LENGTH: 60
(B) TYPE: amino acid
(C) STRANDEDNESS:
(D) TOPOLOGY: linear (xi) SEQUENCE DESCRIPTION: SEQ ID NO: 32:

| Leu | Pro | Met | Tyr | Pro | Ala | Ala | Pro | Leu | Glu | Lys | Met | Phe | Pro | Arg | Val |
| 1 | | | | 5 | | | | | 10 | | | | | 15 | |

| Asn | Pro | Lys | Gly | Ile | Asp | Leu | Leu | Gln | Arg | Met | Leu | Val | Phe | Asp | Pro |
| | | | 20 | | | | | 25 | | | | | 30 | | |

| Ala | Lys | Arg | Ile | Thr | Ala | Lys | Glu | Ala | Leu | Glu | His | Pro | Tyr | Leu | Gln |
| | | 35 | | | | | 40 | | | | | 45 | | | |

| Thr | Tyr | His | Asp | Pro | Asn | Asp | Glu | Pro | Glu | Gly | Glu |
| | 50 | | | | | 55 | | | | | 60 |

(2) INFORMATION FOR SEQ ID NO: 33:

(i) SEQUENCE CHARACTERISTICS:
(A) LENGTH: 345
(B) TYPE: nucleic acid
(C) STRANDEDNESS: double
(D) TOPOLOGY: linear (xi) SEQUENCE DESCRIPTION: SEQ ID NO: 33:

| AAG | CTT | ATG | GGT | GCT | CCT | CCA | AAA | AAG | AAG | AGA | AAG | GTA | GCT | GGT | ATC | 48 |
| Lys | Leu | Met | Gly | Ala | Pro | Pro | Lys | Lys | Lys | Arg | Lys | Val | Ala | Gly | Ile | |

-continued

| 1 | | | | 5 | | | | 10 | | | | | 15 | | | |
|---|---|---|---|---|---|---|---|---|---|---|---|---|---|---|---|---|
| AAT | AAA | GAT | ATC | GAG | GAG | TGC | AAT | GCC | ATC | ATT | GAG | CAG | TTT | ATC | GAC | 96 |
| Asn | Lys | Asp | Ile 20 | Glu | Glu | Cys | Asn | Ala 25 | Ile | Ile | Glu | Gln | Phe 30 | Ile | Asp | |
| TAC | CTG | CGC | ACC | GGA | CAG | GAG | ATG | CCG | ATG | GAA | ATG | GCG | GAT | CAG | GCG | 144 |
| Tyr | Leu | Arg 35 | Thr | Gly | Gln | Glu | Met 40 | Pro | Met | Glu | Met | Ala 45 | Asp | Gln | Ala | |
| ATT | AAC | GTG | GTG | CCG | GGC | ATG | ACG | CCG | AAA | ACC | ATT | CTT | CAC | GCC | GGG | 192 |
| Ile | Asn 50 | Val | Val | Pro | Gly | Met 55 | Thr | Pro | Lys | Thr | Ile 60 | Leu | His | Ala | Gly | |
| CCG | CCG | ATC | CAG | CCT | GAC | TGG | CTG | AAA | TCG | AAT | GGT | TTT | CAT | GAA | ATT | 240 |
| Pro 65 | Pro | Ile | Gln | Pro | Asp 70 | Trp | Leu | Lys | Ser | Asn 75 | Gly | Phe | His | Glu | Ile 80 | |
| GAA | GCG | GAT | GTT | AAC | GAT | ACC | AGC | CTC | TTG | CTG | AGT | GGA | GAT | GCC | TCC | 288 |
| Glu | Ala | Asp | Val | Asn 85 | Asp | Thr | Ser | Leu | Leu 90 | Leu | Ser | Gly | Asp | Ala 95 | Ser | |
| TAC | CCT | TAT | GAT | GTG | CCA | GAT | TAT | GCC | TCT | CCC | GAA | TTC | GGC | CGA | CTC | 336 |
| Tyr | Pro | Tyr | Asp 100 | Val | Pro | Asp | Tyr | Ala 105 | Ser | Pro | Glu | Phe | Gly 110 | Arg | Leu | |
| GAG | AAG | CTT | | | | | | | | | | | | | | 345 |
| Glu | Lys | Leu 115 | | | | | | | | | | | | | | |